United States Patent
Lithgow

(10) Patent No.: US 9,848,791 B2
(45) Date of Patent: Dec. 26, 2017

(54) NEURAL ANALYSIS SYSTEM

(75) Inventor: Brian John Lithgow, Ormond (AU)

(73) Assignee: Monash University (AU)

( * ) Notice: Subject to any disclaimer, the term of this patent is extended or adjusted under 35 U.S.C. 154(b) by 1183 days.

(21) Appl. No.: 13/380,591

(22) PCT Filed: Jun. 24, 2010

(86) PCT No.: PCT/AU2010/000795
§ 371 (c)(1),
(2), (4) Date: Apr. 10, 2012

(87) PCT Pub. No.: WO2010/148452
PCT Pub. Date: Dec. 29, 2010

(65) Prior Publication Data
US 2012/0191002 A1    Jul. 26, 2012

(30) Foreign Application Priority Data
Jun. 24, 2009    (AU) ................... 2009902935

(51) Int. Cl.
*A61B 5/04* (2006.01)
*A61B 5/16* (2006.01)
(Continued)

(52) U.S. Cl.
CPC ...... *A61B 5/04001* (2013.01); *A61B 5/04845* (2013.01); *A61B 5/165* (2013.01);
(Continued)

(58) Field of Classification Search
CPC .................. A61B 5/04001; A61B 5/4082
See application file for complete search history.

(56) References Cited

U.S. PATENT DOCUMENTS

| | | | | |
|---|---|---|---|---|
| 5,419,312 | A | * 5/1995 | Arenberg | A61B 1/00165 600/108 |
| 2005/0273018 | A1 | * 12/2005 | Don | A61B 5/121 600/559 |

(Continued)

FOREIGN PATENT DOCUMENTS

| | | |
|---|---|---|
| WO | WO 02-47547 | 6/2002 |
| WO | WO 2006/024102 | 3/2006 |
| WO | WO 2008/144840 | 12/2008 |

OTHER PUBLICATIONS

Devaiah et al., "Utility of area curve ratio electrocochleography in early Meniere disease", Arch Otolaryngol Head Neck Surg. May 2003;129(5):547-51.*

(Continued)

*Primary Examiner* — Sean Dougherty
(74) *Attorney, Agent, or Firm* — Merchant & Gould P.C.

(57) ABSTRACT

A neural analysis system, including:
 a neural event extractor for generating Sp/Ap curve data and field potential data for background and initial response segments obtained from a person;
 a correlator for correlating the Sp/Ap curve data and field potential data with pathology data for a condition, and generating biomarker data points for axes of a biomarker display; and
 a display module for providing display data to generate the display with the points for use in assessing the person relative to the condition.

19 Claims, 21 Drawing Sheets

(51) Int. Cl.
*A61B 5/00* (2006.01)
*A61B 5/0484* (2006.01)

(52) U.S. Cl.
CPC .......... *A61B 5/4082* (2013.01); *A61B 5/6814* (2013.01); *A61B 5/6816* (2013.01); *A61B 5/6817* (2013.01); *A61B 5/16* (2013.01)

(56) References Cited

U.S. PATENT DOCUMENTS

| | | | | |
|---|---|---|---|---|
| 2008/0167570 | A1* | 7/2008 | Lithgow | A61B 5/0476 600/544 |
| 2009/0312663 | A1* | 12/2009 | John et al. | 600/544 |
| 2010/0261978 | A1* | 10/2010 | Lithgow | A61B 5/04001 600/301 |

OTHER PUBLICATIONS

Lithgow, B.; Shoushtarian, M.; Heibert, D., "Electrovestibulogram (EVestG): The Separation of Benign Paroxysmal Positional Vertigo and Meniere's Disease," Advances in Medical, Signal and Information Processing, 2006. MEDSIP 2006. IET 3rd International Conference on , vol., No., pp. 1,4, Jul. 17-19, 2006.*

Pepe and Thompson. "Combining diagnostic test resutlts to increase accuracy." Biostatistics. 2000. vol. 1, 2, pp. 123-140.*

Shoushtarion et al. "A vestibular diagnostic response." *Australas Phys Eng Sci Med.*, 27(4): 189-98 (2004).

Shoushtarion et al. "The relationship between electrovestibulography and Parkinson's disease severity." 29th *Annual International Conf Proc IEEE Eng Med Biol Soc.* (Aug. 22-26, 2007), 2377-80.

Garrett et al. "Electrovestibulography: the "DC" potentional used to separate Meniere's disease and Benign Paroxysmal Positional Vertifgo." 29th *Annual International Conf. Proc IEEE Eng Med Biol Soc.* (Aug. 22-26, 2007), 2381-2384.

Ferraro et al. "Electrocochleography in the evaluation of patients with Meniere's disease/endolymphatic hydrops." *J. Am. Acad. Audiol*, 17(1): 45-68 (2006).

Hall, James W. III. "Handbook of Auditory Evoked Responses," Allyn and Bacon, Needham Heights, MA, USA (1992).

International Search Report for International Application No. PCT/AU2010/000795 (dated Aug. 10, 2010).

Supplementary International Search Report for International Application No. PCT/AU2010/000795 (dated Apr. 8, 2015).

Haghgooie et al. "Quantitative detection and assessment of schizophrenia using electrovestibulography", *Neural Engineering*, 2009. NER '09. 4th International IEEE/EMBS Conference (Apr. 29, 2009), pp. 486-489.

Lithgow et al. "Electrovestibulogram (EVestG): the separation of benign paroxysmal positional vertigo and Meniere's disease", IET 3rd International Conference on Advances in Medical, Signal and Information Processing, 2006. MEDSIP 2006 (Jan. 1, 2006), pp. 1-4.

* cited by examiner

NEURAL ANALYSIS SYSTEM

This application is a National Stage Application of PCT/AU2010/000,795, filed 24 Jun. 2010, which claims benefit of Serial No. 2009902935, filed 24 Jun. 2009 in Australia and which applications are incorporated herein by reference. To the extent appropriate, a claim of priority is made to each of the above disclosed applications.

FIELD

The present invention relates to a neural analysis system for generating and analysing data indicative of a number of disorders using electrovestibulography.

BACKGROUND

Systems have been developed to obtain an auditory evoked response (AER) or brainstem auditory evoked response (BAER) from a patient that represents activity of the patient's auditory system. The AER is an electrical brain wave or neural response obtained from electrodes placed on the patient in response to a stimulus, normally a sound. Depending on the latency of the response and the placement of the electrodes, different classes or types of AERs can be obtained. Those with the shortest latency are generated by the inner ear and the auditory nerve, and are referred to as electrocochleography ("ECOG" or "ECochG") responses. The next response reflects activity within the auditory brainstem and is referred to as an auditory brainstem response (ABR). Further detail is provided in Hall, James W, III; Handbook of Auditory Evoked Responses; Allyn and Bacon; Needham Heights, Mass., 1992.

Electrocochleography systems are currently used to perform diagnoses of the cochlea and vestibular apparatus. In the case of the vestibular system, recently analysis for this specific part of the ear has been referred to as electrovestibulography (EVestG), being a distinct variant of ECOG. The systems are used to produce a patient neural response which involves placing a recording electrode as close as practical to a patient's cochlea. An acoustic transducer, eg an earphone, can be used to provide an auditory stimulus to evoke the response. For EVestG the patient can be tilted, in different directions, to evoke a specific response from the otoacoustic apparatus, but predominantly the vestibular apparatus. It is not necessary to also use an auditory stimulus for EVestG. A distinct EVestG signal, similar to an ECOG signal but representing the neural response from the predominantly vestibular apparatus, is used to determine an Sp/Ap ratio that can be used for the diagnosis of a number of conditions, particularly Meniere's disease. The first wave, normally labelled N1, of the response signal is examined to determine the summating potential (Sp), the action potential (Ap) and the second summating potential (Sp2), as shown in FIG. 1. The response is only of the order of a few µV and is received with considerable unwanted noise making it difficult to determine and isolate.

International Patent Publication WO 2006/024102 by Monash University describes an ECOG system to extract neural event data that can be used to indicate whether a person has Meniere's, Parkinson's disease or depression. The system produces biological marker data representing the Sp/Ap ratio and a TAP marker that can be used to indicate the presence of a disorder.

International Patent Publication WO 2008/144840, also by Monash University, describes a neural response system for generating biomarker data representing a number of biomarkers for time segments associated with filtered electrovestibulography response signals.

To assist with identification of a wide variety of neurological and neurodegenerative disorders, particularly those associated with the central nervous system (CNS), it would be advantageous to provide at least a useful alternative or in particular an improved system that is able to analyse the neural event data and the biological marker data and produce displays or plots which are able to clearly correlate distinctions in the data obtained to indicate the presence or absence of a condition or disorder in a patient.

SUMMARY

According to one aspect of the present invention there is provided a neural analysis system, including:
  a neural event extractor for generating Sp/Ap curve data and field potential data for background and initial response segments obtained from a person;
  a correlator for correlating the Sp/Ap curve data and field potential data with pathology data for a condition, and generating biomarker data points for axes of a biomarker display; and
  a display module for providing display data to generate the display with said points for use in assessing said person relative to said condition.

According to another aspect of the present invention there is provided a neural analysis system, including:
  a neural event extractor for processing signals representing a response from a person's vestibular apparatus, to generate Sp/Ap curve data and field potential (Ap) loci for time segments;
  a correlator for correlating the Sp/Ap curve data and the Ap loci obtained from a person's right and left sides with average population Sp/Ap curve data and Ap loci to generate first and second correlation data for the Sp/Ap curve data and the Ap loci, respectively; and
  a display module for presenting the first and second correlation data for respective axes of a biometric display.

According to another aspect of the present invention there is provided a neural analysis method, performed by a computer system, including:
  generating Sp/Ap curve data and field potential data for background and initial response segments obtained from a person;
  correlating the Sp/Ap curve data and field potential data with pathology data for a condition to generate biomarker data points for axes of a biomarker display; and
  generating the display with said points for use in assessing said person relative to said condition.

BRIEF DESCRIPTION OF THE DRAWINGS

Preferred embodiments of the present invention are hereinafter described, by way of example only, with reference to the accompanying drawings, wherein.

DETAILED DESCRIPTION

Figure 1:
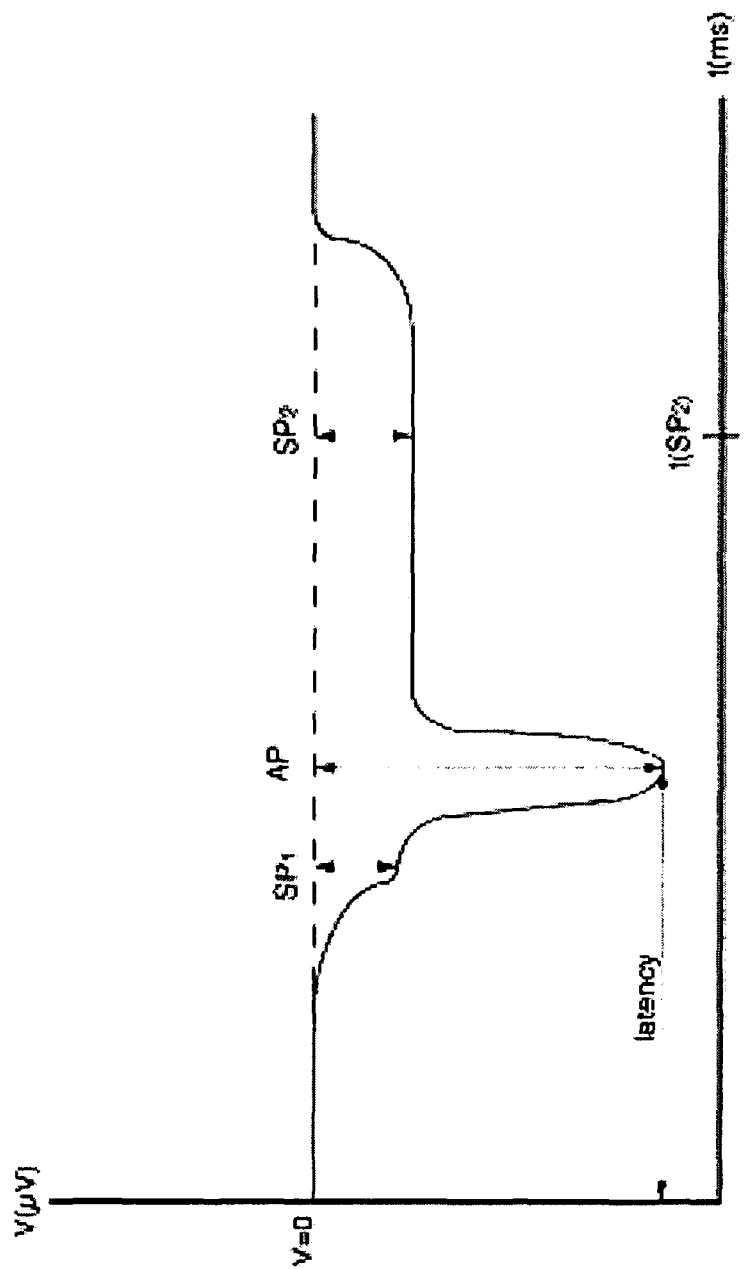
FIG. 1 is a representation of Sp, Ap and Sp2 points related to the first wave of a generalized ECOG response signal from an ECOG system and defines the summating potentials Sp and Sp2 and the action potential Ap.
Figure 2:
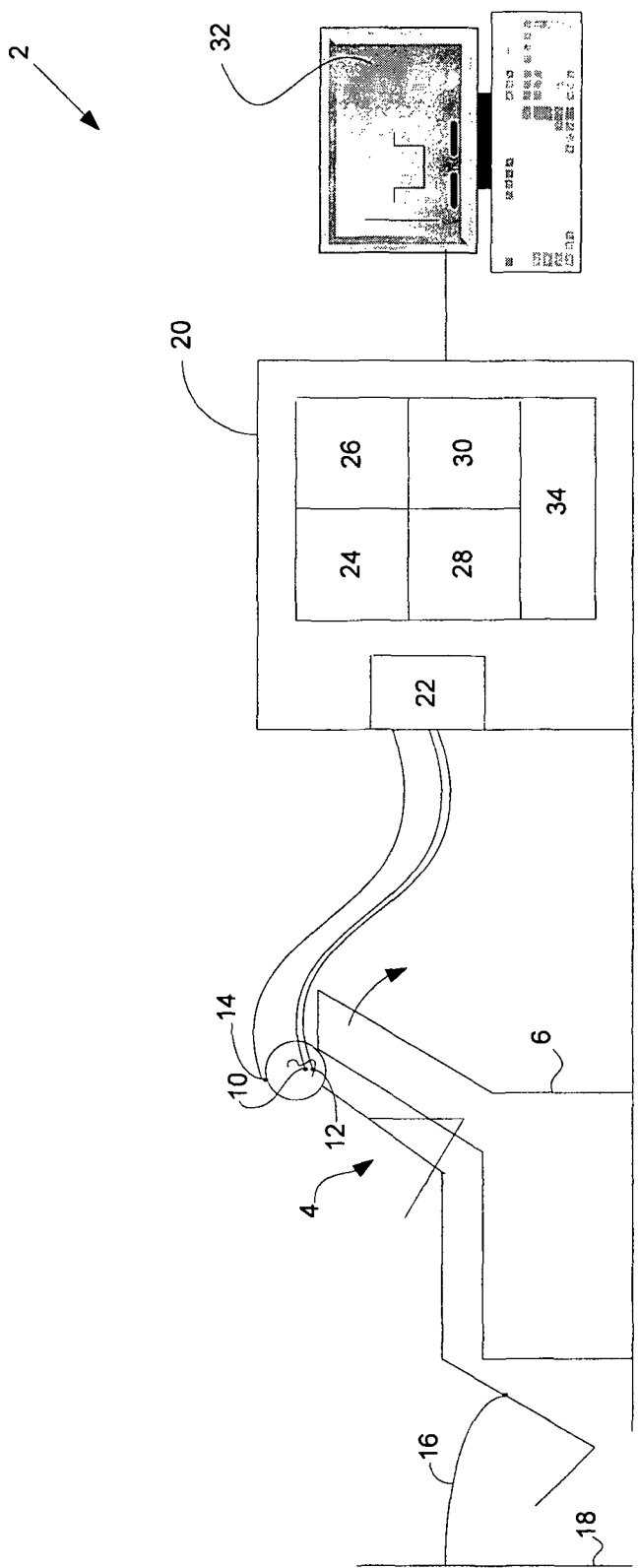
FIG. 2 is a schematic diagram of a preferred embodiment of an EVestG system connected to a patient.

An electrovestibulography (EVestG) system 2, as shown in FIG. 2, provides a neural analysis system that is able to generate biological marker, or biomarker, data representing over 5,000 biomarker measures from a patient 4 subjected to involuntary tilt movements in a tilt chair 6. The biomarker data is generated by signal processing analysis of EVestG signals produced in response to the stimulus provided by the involuntary tilts.

An EVestG signal is obtained from electrodes 10, 12 and 14 electrically connected to an amplifier circuit 22 of a computer system 20 of the system 2. A first electrode 10 (eg a ECochG Electrode produced by Bio-Logic Systems Corp) is placed on the tympanic membrane of an ear of a patient 4. A second electrode 12 is placed on the patient's earlobe, as a reference point, and a third electrode 14 is connected to the patient's forehead and to the common point of the amplifier. A shield connection 16 is also made to an electrical isolation shield 18 normally placed around the testing room. The shield 18 is connected to the shield of the amplifier 22. The testing room is a sound attenuated booth. The booth may include the amplifier 22 with the rest of the computer system 20 placed outside the booth and connected to the amplifier 22 by a USB connection.

The patient 4, as shown in FIG. 2, is placed on the chair 6, such as a recliner lounge chair, that allows the patient's head to rest passively and supported securely to relax the subject during the testing cycle. Electrically powered tilt chairs have been specifically produced by Neuro Kinetics Inc. that enable a patient to be tilted and produce a response to this stimulus which is less corrupted by muscle artefact. An involuntary head tilt can be obtained by an assistant manipulating the chair 6 so as to induce the head tilt without any patient neck muscle activity. Alternatively, the tilt chair can be fitted with and controlled by hydraulic components to invoke a predetermined set of involuntary tilt sequences.

A hydraulically actuated chair 6 is used and configured to ensure stray electric fields caused by the actuation of electrical servo-motors are eliminated as far as possible from being generated in the testing booth. The hydraulically actuated chair is used to provide the tilts without producing either neck muscle artefacts or stray electric fields that may corrupt sensitive signal measurements. To reduce ocular artefacts, the patient is also asked to keep their eyes closed during the testing cycle. The head is tilted down to approximately the same angle as a maximum voluntary head tilt that can be achieved by the patient themself. An EVestG signal or tilt response is obtained for each tilt sequence. The tilts, or tilt sequences, are up/down (patient upright and prone), forward/back, ipsilateral, contralateral, and rotation (patient upright and prone).

Figure 3:
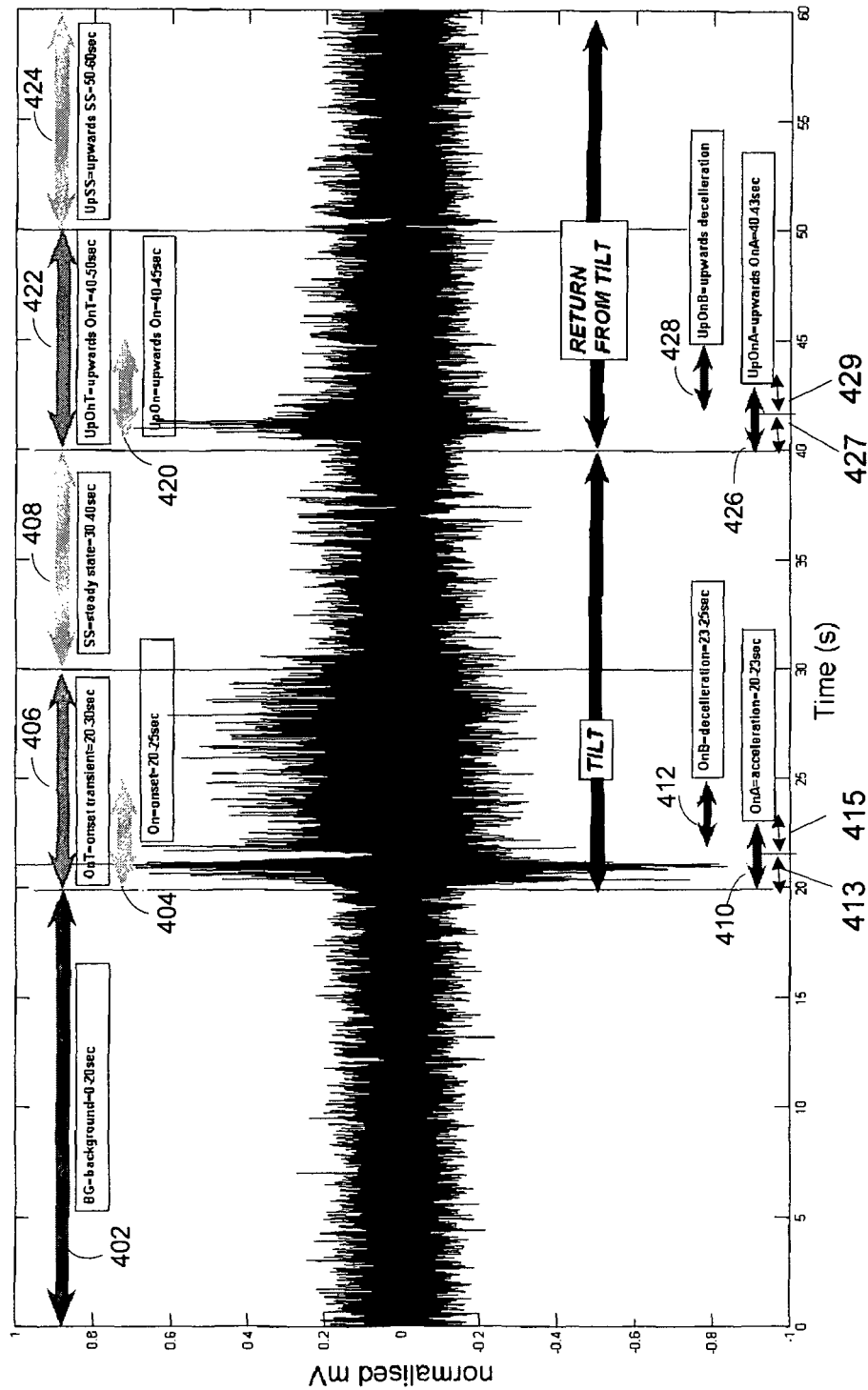
FIG. 3 is a representation of a raw EVestG signal produced by a tilt sequence of the system.

The tilts each produce a raw EVestG response signal, as shown in FIG. 3. The tilt sequences performed by the chair 6 are controlled so that the EVestG response signal obtained is divided into 15 time epochs or segments, but this can be reduced or increased. The neural response produced on electrodes 10 to 14 is continuously recorded by the system 2. The EVestG neural response signal for each tilt is a time domain voltage signal having multiple frequency components. The main components of interest are up to 22,500 Hz. In particular the Sp peak (depending on the signal to noise ratio (S/N)) is only a few samples wide. Accordingly a sampling rate of 44.1 kHz is required during the test cycle as this rate has sufficient sensitivity to recognise and record this event with adequate accuracy by the system 2. This sampling rate can be higher than 44.1 kHZ, and the system 2 would then require faster signal processing components. The seven tilts are performed with two sets of electrodes 10 to 14 positioned respectively for the left ear of the patient and the right ear of the patient. This provides left and right data simultaneously for each ear for each of the seven tilts. Both ears are tested in both dynamic and static phases of all tilt manoeuvres, as a neurological disorder can exist in either hemisphere of the brain, and may only reveal its presence by comparison of each side's response in similar excitatory or inhibitory phases of one or other of the left and right otoacoustic (predominantly vestibular) apparatuses. Such versatility is required if the diagnostic test is to recognise differences in evoked response between each hemisphere of the brain, where in some neurological disorders asymmetry of functioning can occur, (e.g. as for Parkinson's disease).

The sequence for each tilt is to record firstly for 20 seconds with the patient in the tilt chair resting the head/neck against a neck rest and recording a background (BG) signal segment 402 for t=20 seconds. This segment 402 includes a BGi segment which is 1.5 seconds immediately prior to the occurrence of tilt. The patient is then tilted through 45° to come to rest after 2 to 3 seconds. This gives an onset (On) segment 404 for t=20-25 seconds, an onset transient (OnT) segment 406 for t=20-30 seconds, and steady state (SS) segment 408 for t=30-40 seconds. The semicircular canals of the ear function to detect the onset of head movement, and by analysing approximately 5 seconds from a signal recorded at the onset of the head tilt (the On segment) assists with determining the response generated by the semicircular canals. The onset response includes two additional segments, the movement (OnA) segment 410 and the post movement (OnB) segment 412, which occur at t=20-23 seconds and t=23-25 seconds respectively. The OnA segment 410 can be divided to provide an additional OnAA segment 413 for the first 1.5 seconds after tilt and an OnBB segment 415 for the next 1.5 seconds after tilt. The OnAA and OnBB segments are selected to be 20-21.5 and 21.5-23 seconds respectively for increased separation of the acceleration and deceleration components that these segments respectively represent. The times are selected to take into account latency of the hydraulic chair 6 of 0.6-0.8 sec, and can be further subdivided into smaller segments (e.g. 21.5-22.25 and 22.25-23 seconds) for further discrimination. These segments include responses produced predominantly by the semicircular canals and the otolithic organs. The driven semicircular canal response ceases after about 10 seconds, and accordingly the first 10 seconds are therefore considered as the onset transient (OnT) where this decay is observed. The otolith organs, on the other hand, function to maintain static balance, or balance during steady unidirectional movements. The steady state (SS) segment 408 can therefore be analysed to provide the driven response of the otolithic organs separately.

The sequence for the tilt is completed at t=40 seconds by then returning the patient to the original position. The patient is returned to the original position over 1 to 2 seconds and the response produced can again be segmented in a similar manner. The segments for the return part of the tilt sequence:
  (i) Upwards Onset (UpOn) 420 for t=40-45 seconds;
  (ii) Upwards Onset Transient (UpOnT) 422 for t=40-50 seconds;
  (iii) Upwards Steady State (UpSS) 424 for t=50-60 seconds;
  (iv) Upwards Acceleration (UpOnA) 426 for t=40-43 seconds;
  (v) Upwards Deceleration (UpOnB) 428 for t=43-45 seconds;
  (vi) UpOnAA 427 for t=40-41.5 seconds; and
  (vii) UpOnBB 429 for t=41.5-43 seconds.

The upOnAA segment is selected to be 40-41.5 seconds for increased separation of the acceleration component, and the upOnBB segment to be 41.5-43 seconds for increased separation of the deceleration component. Again the times are selected to take into account hydraulic chair latency of 0.6-0.8 sec.

The seven tilt sequences, or tilts, are:
  (i) Up/Down. The chair 6 is moved so as to accelerate the patient's body vertically with patient's head in a normal upright position, and then returned.
  (ii) Up/Down Prone. The chair is moved so as to accelerate the patient's body vertically with the patient's head and body in a prone or lying down position, and then returned.
  (iii) Forward/Back. The patient's body is tilted from a rest position backwards through 25° to 45°, and then returned.
  (iv) Ipsilateral. The patient's body is moved through 25 to 45 degrees ipsilaterally to the electrode 10, and then returned: If the electrode 10 is in the left ear the tilt is to the left then the tilt is back to the right. For the right ear the tilt is to the right.
  (v) Contralateral. The patient's body is moved 25 to 45 degrees contralateral to the electrode 10, and then returned. For instance, if the electrode 10 is in the left ear, the tilt is to the right and the patient is returned. For the right ear the tilt is to the left.
  (vi) Rotation. The patient's body is rotated between 45 and 90 degrees to the right, and then returned, with patient's head in a normal upright position.
  (vii) Rotation Prone. The patient's body is rotated between 45 and 90 degrees to the right, and then returned, with the patient's body in a prone or lying down position.

During all movements the head and neck are not moved relative to the body. The whole body is moved to reduce muscle artefacts. Alternatively, the tilts may be performed by having the subject lie down on their back and tilting their body through ipsilateral, contralateral, vertical and backward directions. These tilts produce fewer muscle artefacts particularly for the ipsilateral and contralateral tilts.

Figure 4:
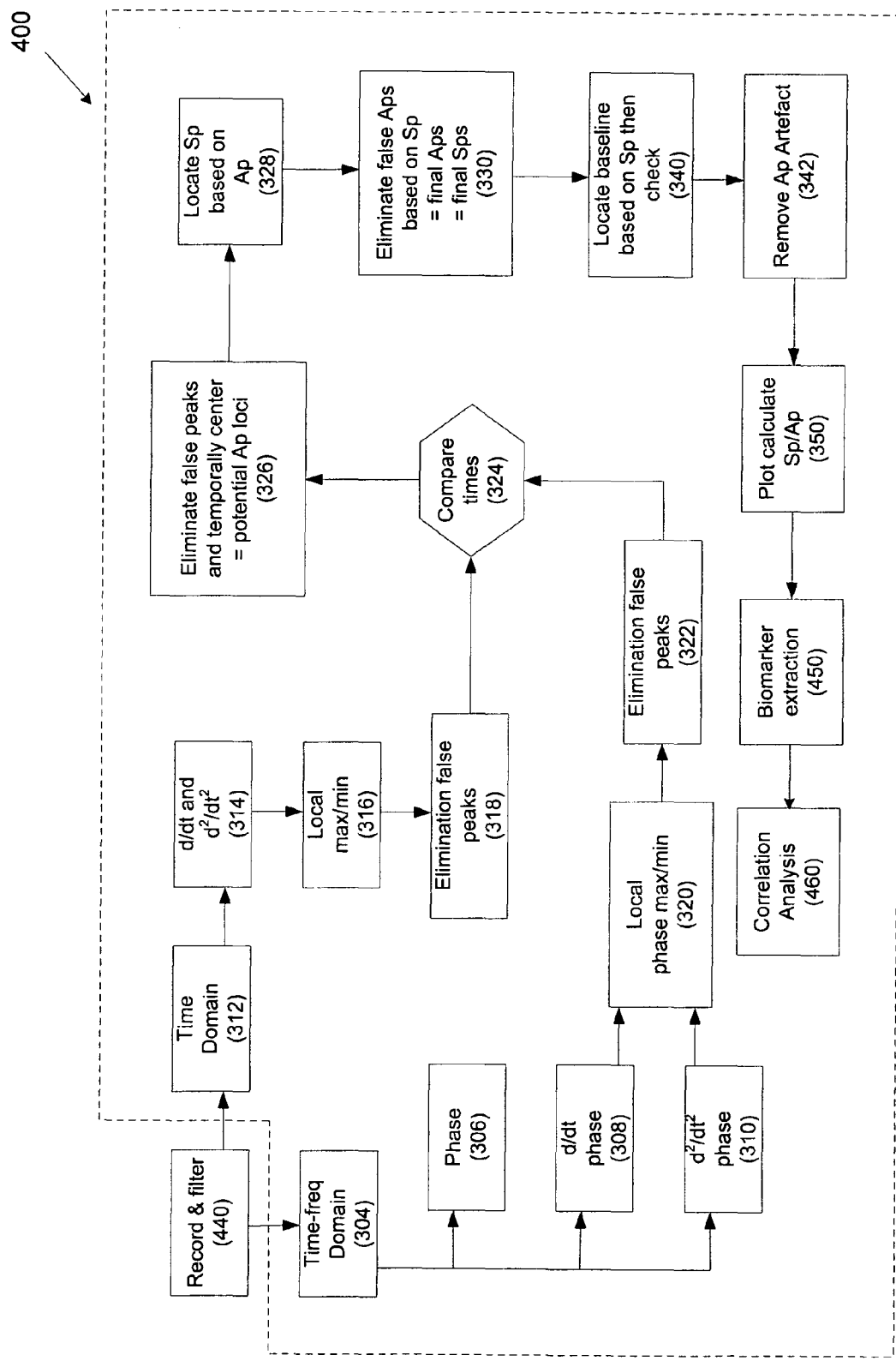
FIG. 4 is a diagram of a neural event extractor and a neural event extraction process performed by an analysis module of the system.

The computer system 20 of the EVestG system 2 includes the amplifier circuit 22 and a communications module 24 for handling the data output of the amplifier 22 and then storing the response as a voltage signal over time as a wave file using a computer program such as Adobe Audition provided by a capture module 26. The amplifier 22 includes a CED 1902 isolated pre-amplifier circuit and a CED Power 1401 analogue-to-digital converter (ADC). Both the CED 1902 and CED 1401 ADC are produced by Cambridge Electronic Design Limited. The CED 1401 ADC has an excellent low frequency (less than 1 Hz) response. The computer system 20 further includes an analysis module 28 and a graphics display module 30. The analysis module 28 provides a neural event extractor 400 and includes computer program code (eg. MATLAB® code) responsible for performing a neural event extraction process (NEEP) of the extractor 400, as shown in FIG. 4, in conjunction with the other software modules. The analysis module 28 also provides a number of different filters used to filter the response signal samples, as discussed below. This filtering may include the removal of the system (or White Noise) response of the feature detection components of the neural event extraction process.

Figure 6:
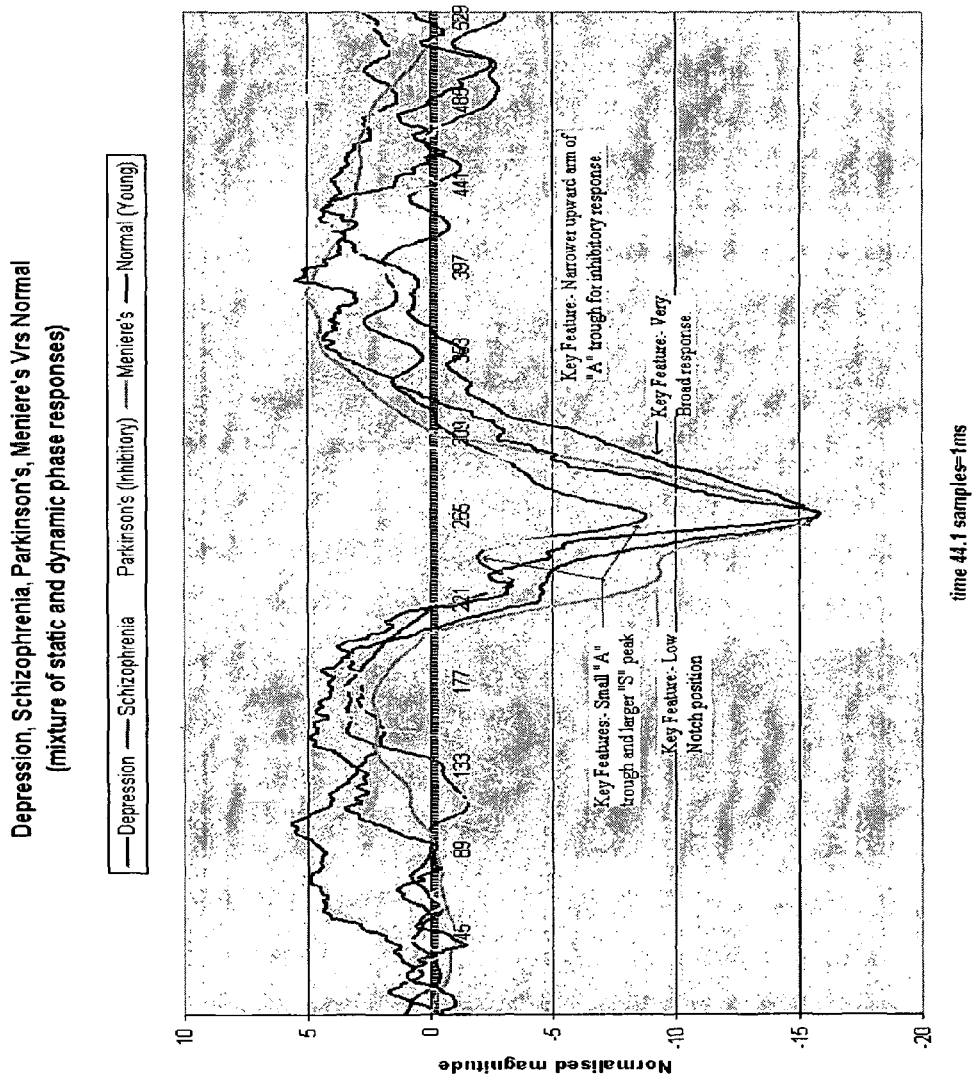
FIG. 6 is a diagram of a Sp/Ap curve generated by the system.

The graphics display module 30 generates a user interface 32 for an operator of the system 2 to provide input controls so that the operator can control the neural event extraction process (NEEP), and to generate displays of neural event data, such as the Sp/Ap plot shown in FIG. 6. The computer program code of the software modules 24 to 30 are stored on memory (such as hard disk, RAM and/or ROM) of the computer system 20 and are run on an operating system 34, such as Microsoft Windows or Linux. The hardware used may include the amplifier circuit 22 and a standard personal computer 20, such as that produced by IBM Corporation. ECOG recording systems are produced by Bio-Logic Systems Corp. Whilst the neural event extraction process (NEEP) may be performed under the control of the software of the modules 24 to 34, it will be understood by a skilled addressee that steps of the process can be performed by dedicated hardware circuits, such as ASICs and FPGAs, and also performed by components or modules distributed across a computer communications network, such as the Internet. For example, dedicated filter circuits can be used to provide the filters, and dedicated digital signal processors (DSPs)

can be used to perform a number of the signal processing steps to enhance the processing speed.

Figure 5:
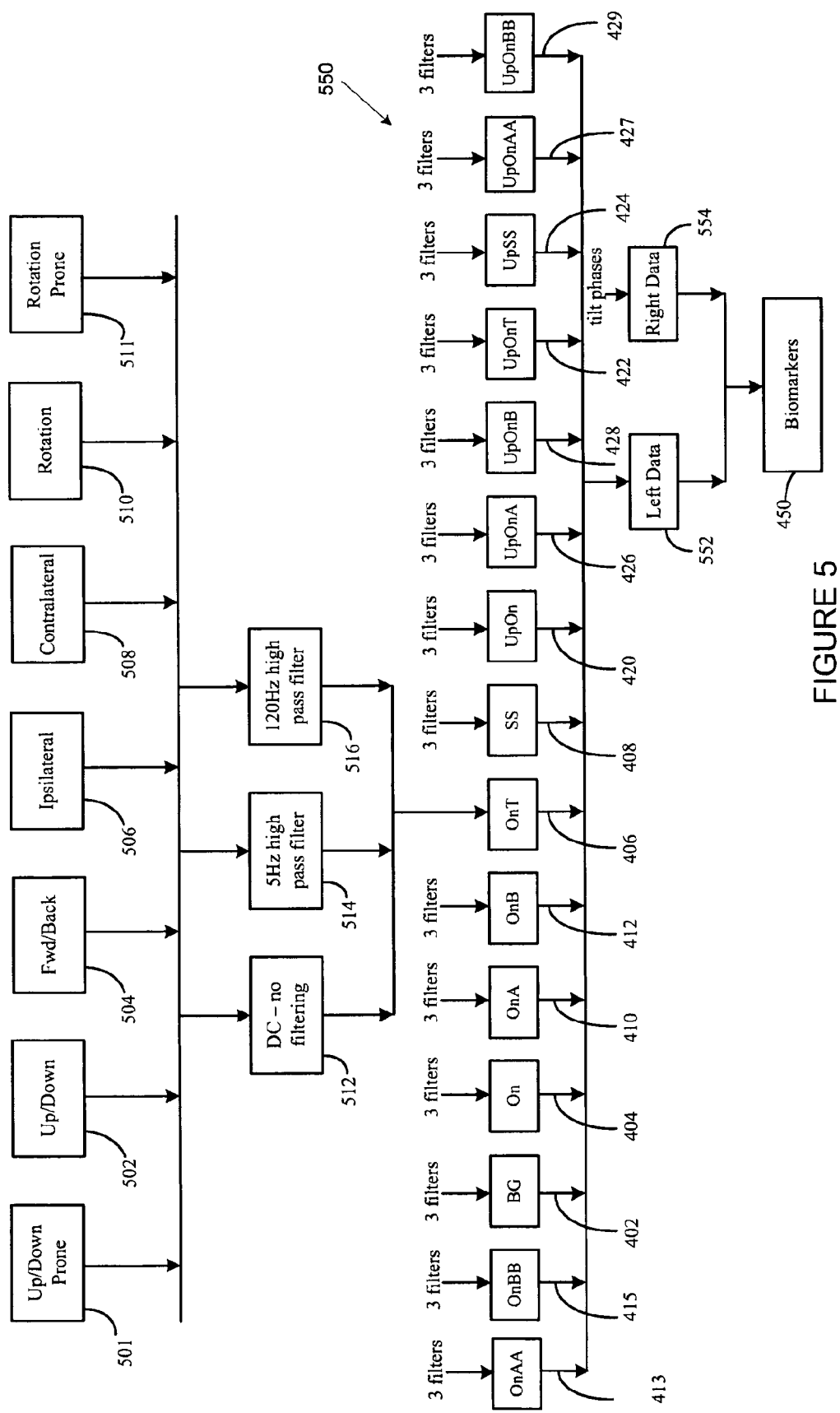
FIG. 5 is an architecture diagram of filters and a segmentation component of the system.

The neural event extraction process (NEEP), as shown in FIG. 4, is the same as that described in WO 2006/024102 for an EVestG response, except for the recording filtering, and segmenting process 440, the biomarker extraction process 450 and a correlation analysis process 460. The data representing the EVestG responses obtained from each of the seven tilts and for each ear of a patient, i.e. 14 responses, is recorded, as discussed above, and then filtered three different ways to provide filtered data for three filtered responses for each tilt response, i.e. filtered response data for 42 filtered tilt responses. A shown in FIG. 5, the tilt responses of each tilt 501, 502, 504, 506, 508, 510 and 511 are each filtered by a first filter 512, a second filter 514 and a third filter 516. The first filter 512 provides no filtering, as it allows all frequencies to pass, including the data representing DC voltage levels. It does, however, include a very narrow notch filter which introduces no phase shifts but removes power line harmonics, e.g. at 50 Hz or 60 Hz, and also removes hydraulic (proportional valve) switching artefacts that may be introduced by hydraulic actuation of the chair. This notch filter is also employed at the output of the second and the third filters 514 and 516. The second and third filters 514 and 516 both provide high pass filtering. The second filter 514 includes a 5 Hz high pass filter and the third filter 516 includes a 120 Hz high pass filter. Providing the three filtered tilt responses produced by the filters 512, 514 and 516 for processing by a neural event extraction process (NEEP) gives the benefit that groups of biological markers that can be corrupted by low frequency data are enhanced in the high pass filtered responses, whereas other critical biological markers that are only present or can only be extracted when the low frequency data is present are also available, e.g. some biological markers used for Meniere's disease.

The 42 filtered tilt responses are each segmented by a segmentation process 440 performed by segmenter 550 of the analysis module 28 in order to produce the fifteen segments 402, 404, 406, 408, 410, 412, 413, 415, 420, 422, 424, 426, 427, 428 and 429 for each filtered tilt response, as discussed above. This produces 630 sets of data representing 630 filtered tilt response segments. The segments comprise data obtained from the left ear of the patient 552 and data obtained from the right ear of the patient 554. The output of the record, filter and segmentation process 440 is the 630 filtered tilt response signals that are each then subjected to the remaining processes of the neural event extraction process (NEEP) shown in FIG. 4. This produces Sp/Ap data for each segment, i.e. for each of the 630 sets of data. The segments are each treated as an EVestG response by the neural event extraction process (NEEP). As discussed in WO 2006/024102, the process decomposes each response segment using a complex Morlet wavelet to obtain phase data across seven equally logarithmically space scales from 600 Hz to 12 KHz. The scale data is processed to determine loci where sharp changes in phase occur across all scales.

However, a large phase change may be indefinable across the scales but at more than one (or slight variations in) sample time. At scale 1, for example, a locus could be found at say time sample 344. For scale 2 the loci might be at sample 345, scale 3 at loci 347, scale 4 loci 349, scale 5 loci 346, scale 6 loci 345 etc. This represents a curved connection of points across the scales relating the same phase change. To cater for this the NEEP allows for and applies an acceptable gap between scale sample times. This gap may be arbitrarily set, but is typically 1 to 3 samples.

Once these loci are discriminated, characteristic data for a Sp/Ap plot is derived and used to select neural responses from artefacts. The data for a Sp/Ap curve is determined by averaging the loci determined across the scales, and an EVestG plot can be produced from the data for each segment as shown in FIG. 6.

The neural event extraction process (NEEP) can inadvertently detect loci due to White noise. To address this and improve the S/N ratio of the extracted EVestG Sp/Ap plot the white noise response can be subtracted by the system 2. The system 2 achieves this by first inputting white noise filtered to match the recording characteristics of the system (eg. 10 kHz low pass and no (DC), 5 or 120 Hz high pass filtering) and recording the EVestG Sp/Ap system response to this input, which is stored as a Band Limited White Noise (BLWN) response. A scaled BLWN response is then subsequently subtracted from the EVestG (RAEVestG) produced by the NEEP. The scaling factor is decided by determining the Ap point of the RAEVestG. The scaling factor is set to 0 and incremented in 0.01 steps until the Output data=RAEVestG minus the scaled BLWN response sees the Ap point (response plot minima) shifting by more than an arbitrary time, typically 2 samples. Once subtracting the scaled BLWN response causes a marked adjustment in the position of the Ap point, the scaling factor (scale) is set and not increased any further. This gives an adjusted NEEP Output EVestG=RAEVestG−scale*BLWN. The BLWN response is produced by the NEEP processing the white noise response with the threshold in step 318 set so that significant field potentials are detected to characterise the BLWN response.

Sometimes neural events (field potentials) occur so that their waveforms overlap. When this occurs the diagnostic biomarkers can become corrupted. To solve this problem the neural event extraction process (NEEP) can exclude such events without loss of biomarker integrity. To find these events the loci of the Ap points are determined. If these loci are closer than an arbitrary number of samples typically 66 samples (1.5 ms) both field potentials can be excluded. A flag can be set or reset so that the exclusion decision can be switched in or out as part of the NEEP processing.

Figure 7:
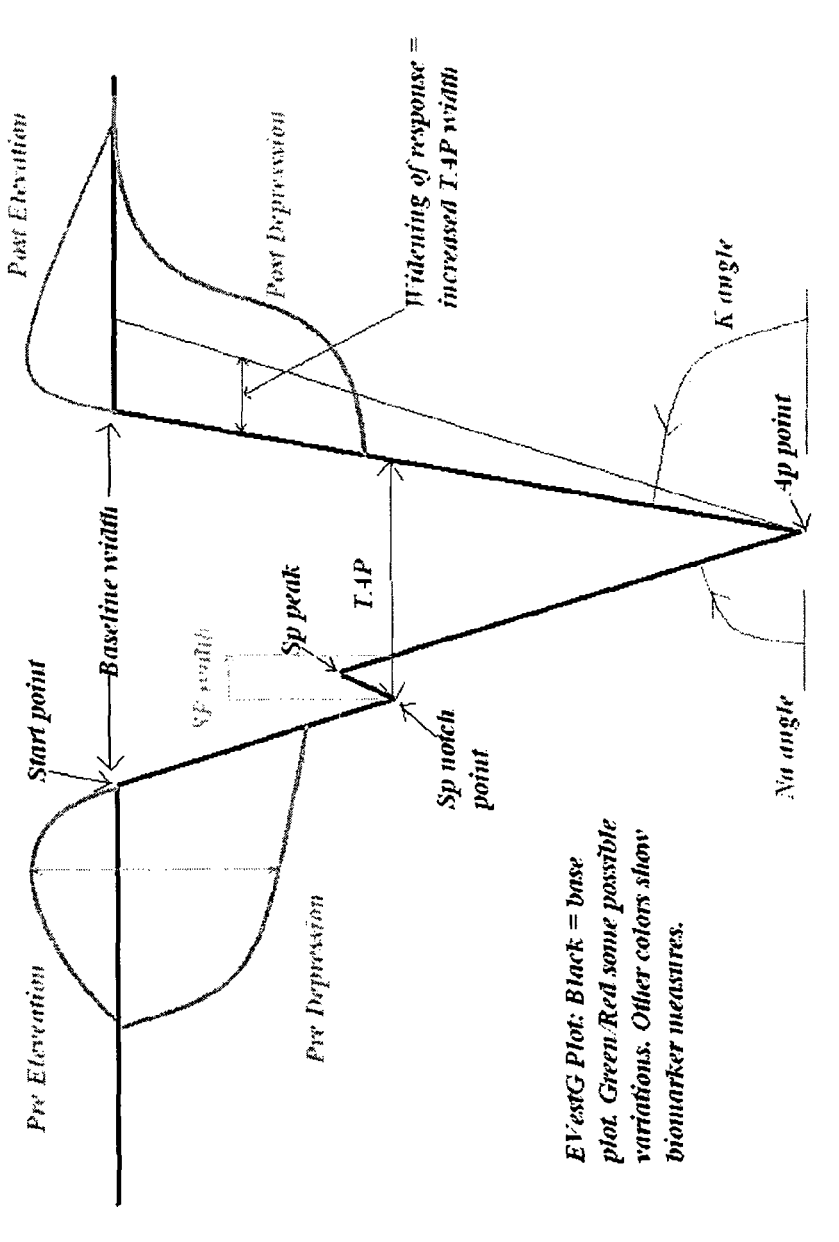
FIG. 7 is a schematic diagram of biomarkers obtained from data associated with an EVestG plot.

Once the Sp/Ap or EVestG curve data is produced for each segment (350), the extraction process is able to invoke a biomarker extraction process (450) on each segment that generates metric data or biological marker data representing 17 different biological markers. As there are 630 different segments produced for each patient, this gives rise to biological marker data representing 630 measures of each biomarker. Accordingly, the biomarker data for each patient represents 10,710 biomarker measures. This is a considerable amount of data obtained from one patient subjected to the seven tilt sequences and can be used to accurately determine the presence or not of a wide variety of neurological and neurodegenerative disorders. The 17 biological markers are as defined below and illustrated in FIG. 7 (and given the definitions: Ap is the whole V shaped EVestG curve; and the Ap point is the lowest point of the Ap plot):

(i) Pre Ap Elevation or Depression. An elevation or depression above/below the baseline immediately preceding the Ap.

(ii) Post Ap Elevation or Depression. An elevation or depression above/below the baseline immediately after the Ap.

(iii) Ap Magnitude. The voltage magnitude at the Ap point.

(iv) Sp notch point (loci). The time at which the downward arm of the Ap reverses/slows/stops, typically about 0.3 ms after Ap onset.
(v) Start point (loci). The time of commencement of the Ap.
(vi) Baseline width. The width of the Ap at the baseline level.
(vii) Sp peak. The tip of the short rise after the Sp notch point before the continuation downwards of the Ap towards the Ap lowest point.
(viii) Sp width. The width (time) from the Sp notch to the next downward arm of the Ap.
(ix) Sp Magnitude. The height of the Sp peak above the Sp notch point.
(x) TAP (internal). The width (time) of the Ap at the Sp notch level measured from the downward arm of the Ap after the Sp notch horizontally to the upward arm of the Ap.
(xi) TAP (notch). The width (time) of the Ap at the Sp notch level measured from the Sp notch horizontally to the upward arm of the Ap.
(xii) Na angle. The angle of the downward arm of the AP between the Ap lowest point and the height of the Sp notch measured from vertical to that arm.
(xiii) K angle. The angle of the upward arm of the AP between the Ap lowest point and the height of the Sp notch measured from vertical to that arm.
(xiv) Na+K angle. Sum of the eleventh and twelfth biomarker values.
(xv) Sp/Ap ratio. Vertical distance from Sp notch to baseline divided by vertical distance from Ap point to baseline.
(xvi) Spike Rate. The number of field potentials detected and used to form the Ap plot.
(xvii) DC Shift. The vertical shift between different Ap plots measured from the baseline level.

An additional two biomarkers for each of the 42 filtered tilt response signals is obtained by subtracting the data obtained in the OnAA and OnBB segments from the BGi segment for each response signal. This produces:
(a) BGi-OnAA response data, and (b) BGi-OnBB response data.

This produces 84 additional biomarkers representing the dynamic response of each of the respective tilt response signals.

Figure 8:
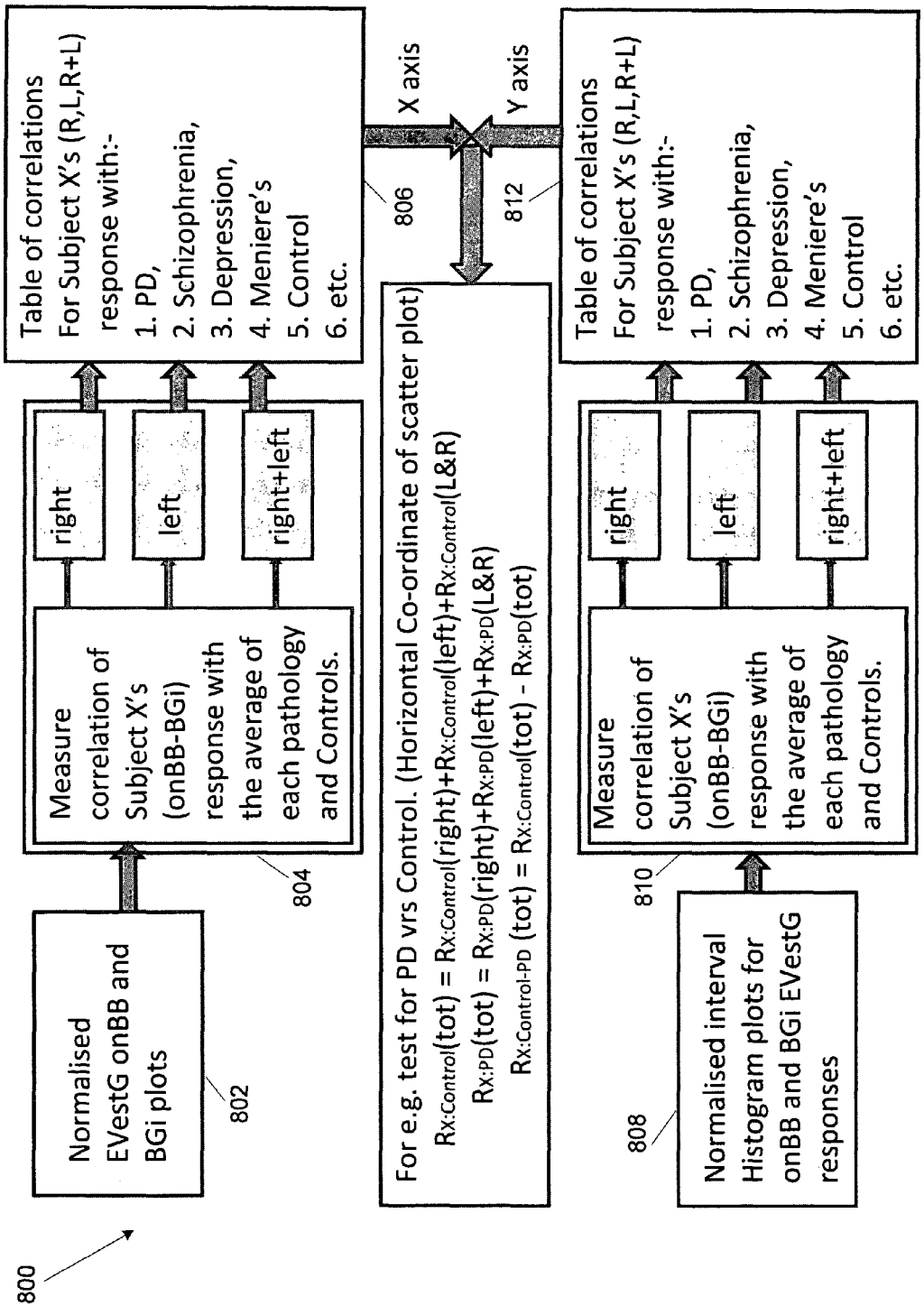
FIG. 8 is a diagram of a neural analysis process performed by the analysis module of the system.
Figure 9:
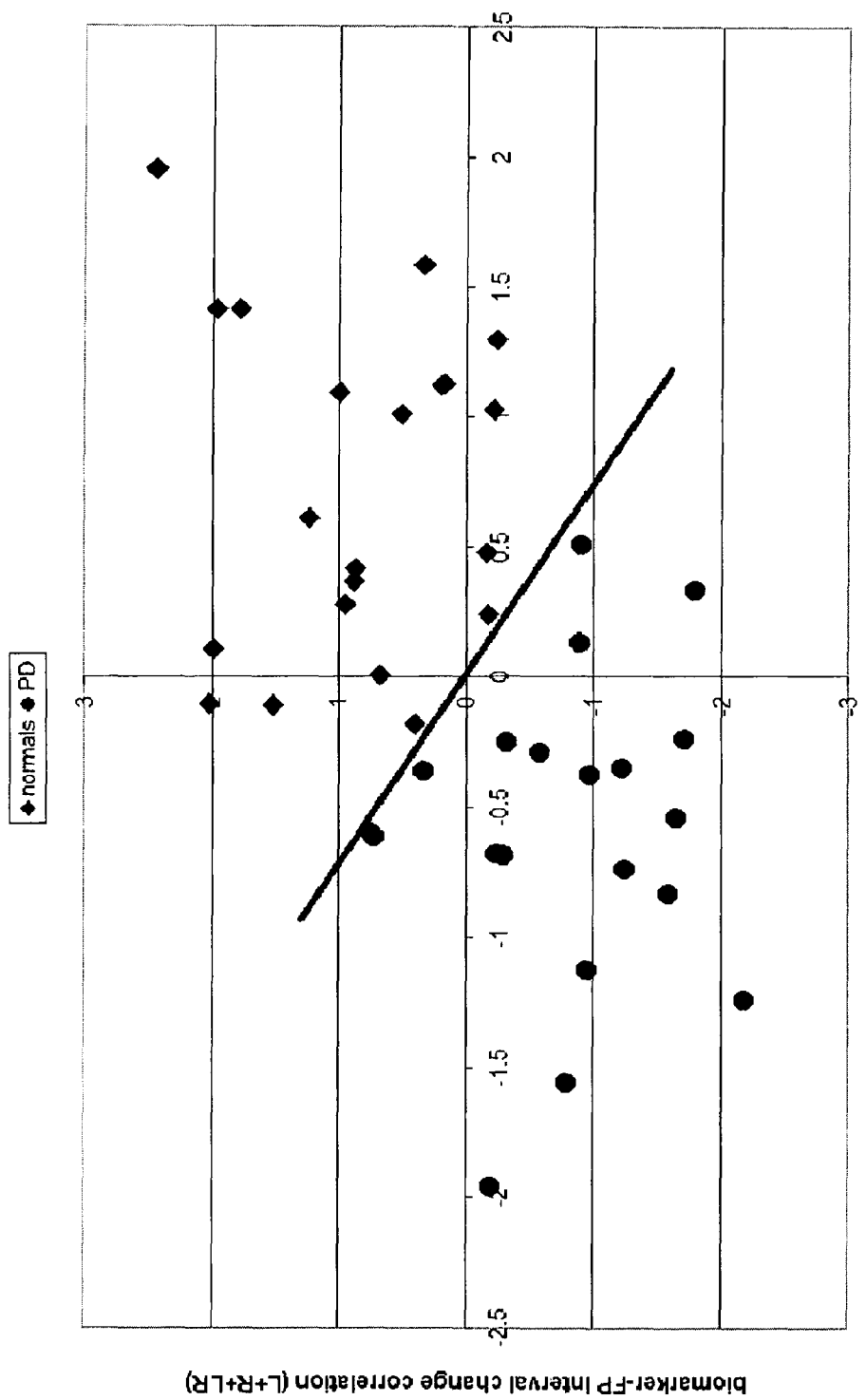
FIG. 9 is a diagram of a biomarker display generated by the EVestG system for patients with Parkinson's disease.

The analysis module 28 includes a correlation analysis component 800, as shown in FIG. 8, which performs an analysis process 460 to generate display point data for each axis of condition diagnosis biomarker displays generated by the graphics display module 30. The component 800 processes the EVestG curve data to generate plot point data for one axis of a biomarker display, and processes time response data to generate plot point data for another axis of the biomarker display. An example of a biomarker display is shown in FIG. 9 and other displays are shown in FIGS. 10 to 21 discussed below. Each point shown on the display represents a patient or test subject. The position of the patient's point in the display indicates the presence or absence of a CNS condition or the relative response by the patient to a particular treatment or dosage regime for that condition.

For the horizontal axis of the display, the biomarker data used is the EVestG curve data for the BGi (immediate background t=18.5-20 sec) and on BB (deceleration phase of tilt t+21.5-23 sec) tilt phases/segments. Rather than using the data for all three filters, the data for the DC filter for these two segments is used. The DC data contains all the lowest frequency components of the response i.e. the components occurring over longer time frames and is reflective of more cortical inputs and time frames. The BGi segment is used as it reflects the immediate state prior to the tilt and there are low frequency (long time frame) fluctuations in background level. The on BB segment is used as it shows a large response change compared to background. The component 800 executes the following signal processing steps:

(1) The max and minimum values of the on BB and BGi Sp/Ap plots are determined by processing a data time sample range 305:441 and 441:537 of the Sp/Ap plots where sample 441 corresponds to the Ap point (corresponding to point 265, as shown in FIG. 6) to cover the entire range from Pre Elevation and Depression to Post Elevation and Depression in order to determine the range of the response above the baseline and to the Ap point. Each Sp/Ap plot includes 881 time sample points. Based on the larger range (on BB or BGi) the plots are normalised by dividing by this range. The largest range in data values is considered 100% (normally the range of the on BB plot is bigger than that of the BGi plot) so this is taken to be the normal and the other scaled by it.

(2) The normalised BGi and on BB plots are subtracted to generate data representing BGi-on BB plots.

(3) For each patient (age and gender matched population) group an average BGi-on BB plot is generated for the ipsilateral and contralateral tilt sequences and the right data, left data and right plus left response data obtained from each member of the group. This produces 6 average plots for each population group (i.e. 2 tilts each for left, right and left+right data). Each population represents either a control group or group representing a pathology or a condition the group is known to possess, i.e. Parkinson's Disease (PD), Schizophrenia, Depression, Meniere's Disease, etc. The 6 plots per population can be obtained in advance and are used to obtain correlation measure data for a patient or subject "X".

(4) Subject X's six normalised BGi-on BB plot responses (all 881 time sample points) are compared with the respective 6 average plots for a control group or a pathology. The responses are obtained from the left data, right data and right+left data for the ipsilateral and contralateral tilts. These tilts are used as they generate the largest response differences from resting or from each other. Ipsilateral tends to be excitatory and contralateral inhibitory, especially from the semicircular canals of the vestibular apparatus. Each comparison generates a correlation measure using a correlation function. The correlation function generates a correlation coefficient R as the measure using the points of two compared plots. A number of different correlation functions can be used to provide the coefficient R. For example, $$R = Correl(X, Y) = \frac{\sum (x - \bar{x})(y - \bar{y})}{\sqrt{\sum (x - \bar{x})^2 \sum (y - \bar{y})^2}}$$

where $\bar{x}$ and $\bar{y}$ are the sample means of the points x and y of each compared plot X and Y, respectively.

(5) The 6 coefficients obtained are summed together to provide correlation data representing the comparison with subject X and a control population or pathology population. The values for the correlation data for a control and a pathology are subtracted to form the horizontal plot point data for subject X on a scatter plot of a biometric display. For example, to obtain a point for Parkinson's Disease (PD) versus Control (Horizontal Co-ordinate of scatter plot):

$$R_{X:Control}(tot)=R_{X:Control}(\text{right})+R_{x:Control}(\text{left})+R_{X:Control}(L\&R);$$

the correlation data for X representing a measure of similarity with the control population;

$$R_{X:PD}(tot)=R_{X:PD}(\text{right})+R_{x:PD}(\text{left})+R_{X:PD}(L\&R);$$

the correlation data for X representing a measure of similarity with the PD population; and $$\text{Horizontal point}=R_{X:control-PD}(tot)=R_{X:control}(tot)-R_{x:PD}(tot).$$

If the value of the horizontal point is positive, this provides a measure of the association of X with the control population. If it is negative, this provides a measure of the association of X with PD's Referring to FIG. 8, the correlation analysis component 800 performs a normalisation process 802 on the Sp/Ap (EVestG) plots which involves steps (1) and (2) described above, a correlation process 804 which involves steps (3) and (4) described above, and a coefficient process 806 which involves step (5) and storing and processing the coefficients to generate the points for the x axis of a biomarker display.

For another axis, e.g. the vertical or y axis of the biometric display, the biomarker data is generated from the recorded times of each extracted field potential (i.e. Ap loci) determined by the NEEP at step 330. For a given segment there may be over 300 Ap points detected. Using the signals obtained from the 120 Hz filter 516 (to remove unwanted DC artefacts) the field potential (Ap) times are used to generate an interval histogram for the BGi (immediate background t=18.5-20 sec) and on BB (deceleration phase of tilt t=21.5-23 sec) tilt phase segments. The intervals determined are the time differences between adjacent Ap loci in the segments. The correlation process 460 uses 25 time bins (<0.5 ms, 0.5-0.6, 0.6-0.71, 0.71-0.8, 0.8-1, 1-1.2, 1.2-1.4, 1.4-1.62, 1.62-2, 2-2.3, 2.3-2.8, 2.8-3.3, 3.3-5, 5-6, 7.1, 7.1-8, 8-10, 10-12, 12-14, 14-16.2, 16.2-20, 20-23, 23-28, 28-33, 33-50 ms) to generate a histogram for each tilt phase segment. The signal processing steps include:

(6) The interval histograms are generated and each is normalised to represent a percentage of the number of field potential intervals (Ap points) in the segment response, i.e. the total number of final Ap points is 100%.
(7) The normalised BGi and on BB histograms are subtracted to give a BGi-on BB histogram with 25 points.
(8) An average BGi-on BB interval histogram is created for the ipsilateral and contralateral right, left and right plus left (or left-right) responses for each age and gender matched population group. Again, each population represents either a control group or group representing a pathology or a condition the group is known to possess, i.e. Parkinson's Disease (PD), Schizophrenia, Depression, Meniere's Disease, etc. These 6 histograms per population can be obtained in advance and are used to obtain correlation measure data for a patient or subject "X".
(9) Subject X's six BGi-on BB interval histograms (having 25 point values for each histogram) are compared respectively with the 6 average interval histograms for a control group or a pathology. The interval histograms are obtained from the left data, right data and right+left data for the ipsilateral and contralateral tilts. Each comparison generates a correlation measure using a correlation function. The correlation function generates a correlation coefficient R as the measure using the points of two compared histograms. A number of different correlation functions can be used to provide the coefficient R. For example, $$R = Correl(X, Y) = \frac{\sum (x-\bar{x})(y-\bar{y})}{\sqrt{\sum (x-\bar{x})^2 \sum (y-\bar{y})^2}}$$

where $\bar{x}$ and $\bar{y}$ are the sample means of the points x and y of each compared histogram X and Y, respectively.
(10) The 6 coefficients obtained are summed together to provide correlation data representing the comparison with subject X and a control population or pathology population. The values for the correlation data for a control and a pathology are subtracted to form the vertical plot point data for subject X on a scatter plot of a biometric display. For example, to obtain a point for PD versus Control (Vertical Co-ordinate of scatter plot):

$$R_{X:Control}(tot)=R_{X:Control}(\text{right})+R_{x:Control}(\text{left})+R_{X:Control}(L\&R);$$

the correlation data for X representing a measure of similarity with the control population;

$$R_{X:PD}(tot)=R_{X:PD}(\text{right})+R_{x:PD}(\text{left})+R_{X:PD}(L\&R);$$

the correlation data for X representing a measure of similarity with the PD population; and $$\text{Vertical point}=R_{X:control-PD}(tot)=R_{X:Control}(tot)-R_{x:PD}(tot).$$

If the value of the vertical point is positive, this provides a measure of the association of X with the control population. If it is negative, this provides a measure of the association of X with PD.

Referring to FIG. 8, the correlation analysis component 800 performs a normalisation process 802 on the OnBB and BGi interval histograms for the EVestG responses for those segments, which involves steps (6) and (7), described above. A correlation process 810, which involves steps (8) and (9) described above, is performed to obtain the correlation coefficients for subject X using the interval histograms, and a coefficient process 812, which involves step (10) includes storing and processing the coefficients to generate the points for the y axis of a biomarker display.

The correlation component 800 can also be used to obtain biomarker data for a third axis of the display, e.g. the z axis, using the correlation analysis process 460 to further improve separation and discrimination between patients. For this axis a spectral density plot or spectrogram is generated using 32-512 point Fast Fourier Transform (FFT) applied across the Sp/Ap plot of one or a combination of the on BB, BGi or BGi-on BB responses. The signal processing steps include:

(11) Each spectrogram is normalised so the total bin size sums to 100%.
(12) The normalised BGi and on BB spectrograms are subtracted to provide a BGi-on BB spectrogram.
(13) Average BGi, on BB and BGi-on BB spectrograms are created for the ipsilateral and contralateral right, left and right plus left responses for each age and gender matched population group. Again, each population represents either a control group or group representing a pathology or a condition the group is known to possess, i.e. Parkinson's Disease (PD), Schizophrenia, Depression, Meniere's Disease, etc. These 18 spectrograms per population can be obtained in advance and are used to obtain correlation measure data for a patient or subject "X".

(14) Subject X's six BGi-on BB spectrograms are compared respectively with the 6 average BGi-OnBB spectrograms for a control group or a pathology. The spectrograms are obtained from the left data, right data and right+left data for the ipsilateral and contralateral tilts. Each comparison generates a correlation measure using a correlation function. The correlation function generates a correlation coefficient R as the measure using the points of two compared spectrograms. A number of different correlation functions can be used to provide the coefficient R.

For example, $$R = Correl(X, Y) = \frac{\sum (x - \bar{x})(y - \bar{y})}{\sqrt{\sum (x - \bar{x})^2 \sum (y - \bar{y})^2}}$$

where $\bar{x}$ and $\bar{y}$ are the sample means of the points x and y of each compared spectrogram X and Y, respectively.

(15) The coefficients obtained are summed together to provide correlation data representing the comparison with subject X and a control population or pathology population. The values for the correlation data for a control and a pathology are subtracted to form the vertical plot point data for subject X on a scatter plot of a biometric display. For example, to obtain a point for PD versus Control (z co-ordinate of scatter plot):

$$R_{X:control}(tot) = R_{X:control}(right) + R_{X:control}(left) + R_{X:control}(L\&R);$$

the correlation data for X representing a measure of similarity with the control population;

$$R_{X:PD}(tot) = R_{X:PD}(right) + R_{X:PD}(left) + R_{X:PD}(L\&R);$$

the correlation data for X representing a measure of similarity with the PD population; and $$Z\ point = R_{X:Control-PD}(tot) = R_{X:Control}(tot) - R_{X:PD}(tot).$$

If the value of the Z point is positive, this provides a measure of the association of X with the control population. If it is negative, this provides a measure of the association of X with PD.

Another biomarker that can be used for example in depression or schizophrenia separation is the average of the Sp/Ap plot for a patient in regions 100-150 samples either side of the Ap plot and combinations thereof.

Figure 10:
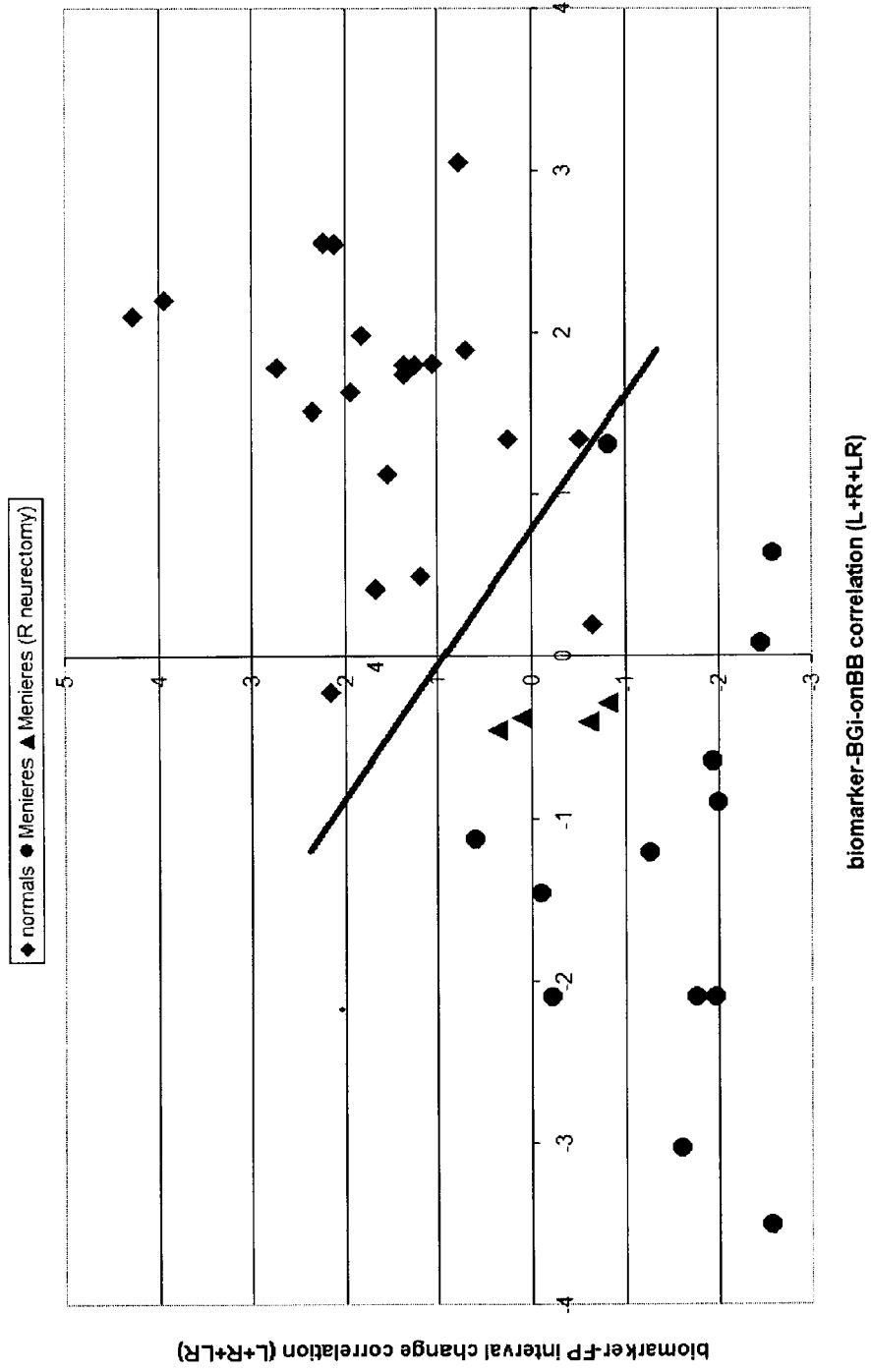
FIG. 10 is a diagram of a biomarker display generated by the EVestG system for patients with Meniere's disease.
Figure 11:
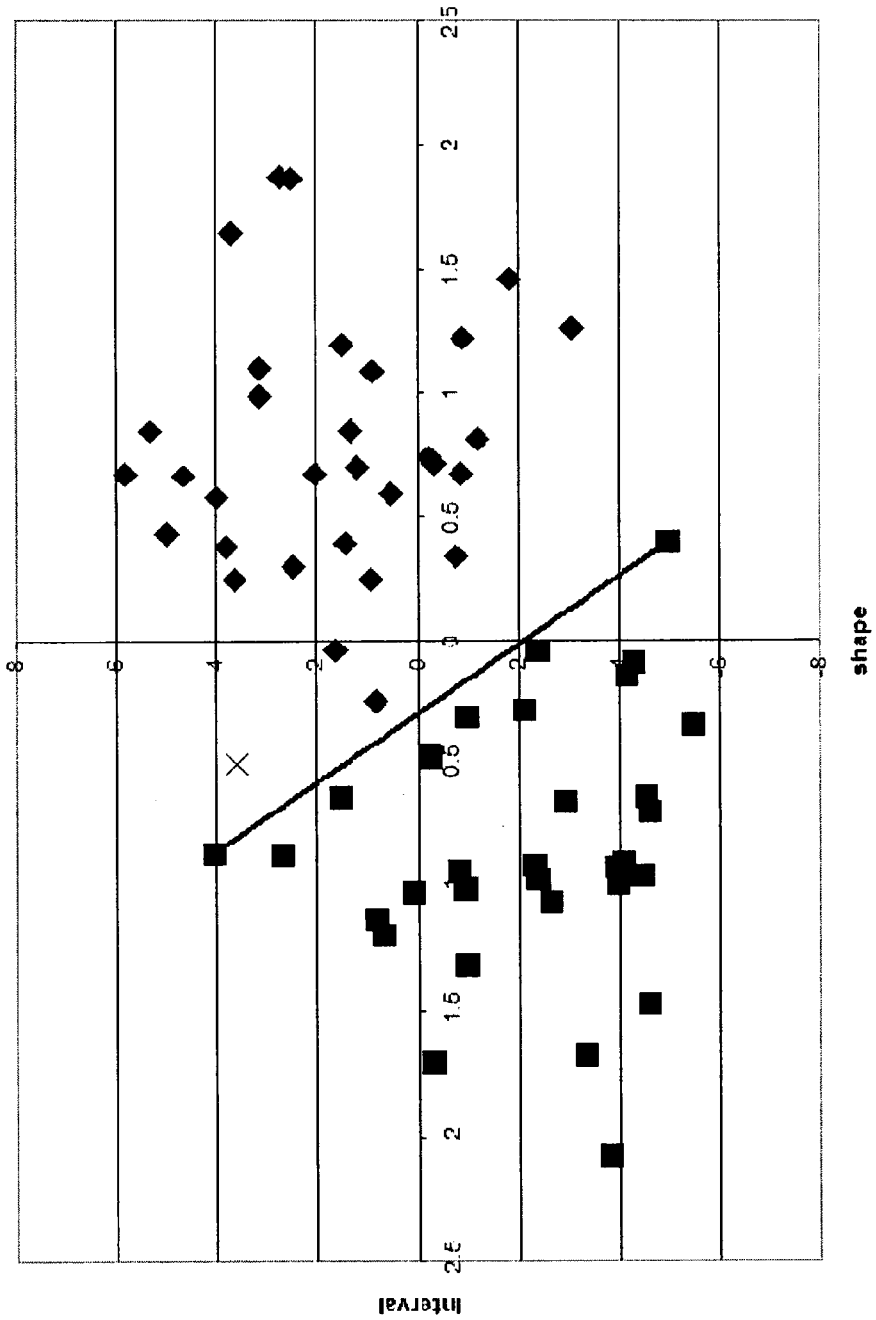
FIG. 11 is a diagram of a biomarker display generated by the EVestG system for patients with Schizophrenia.
Figure 12:
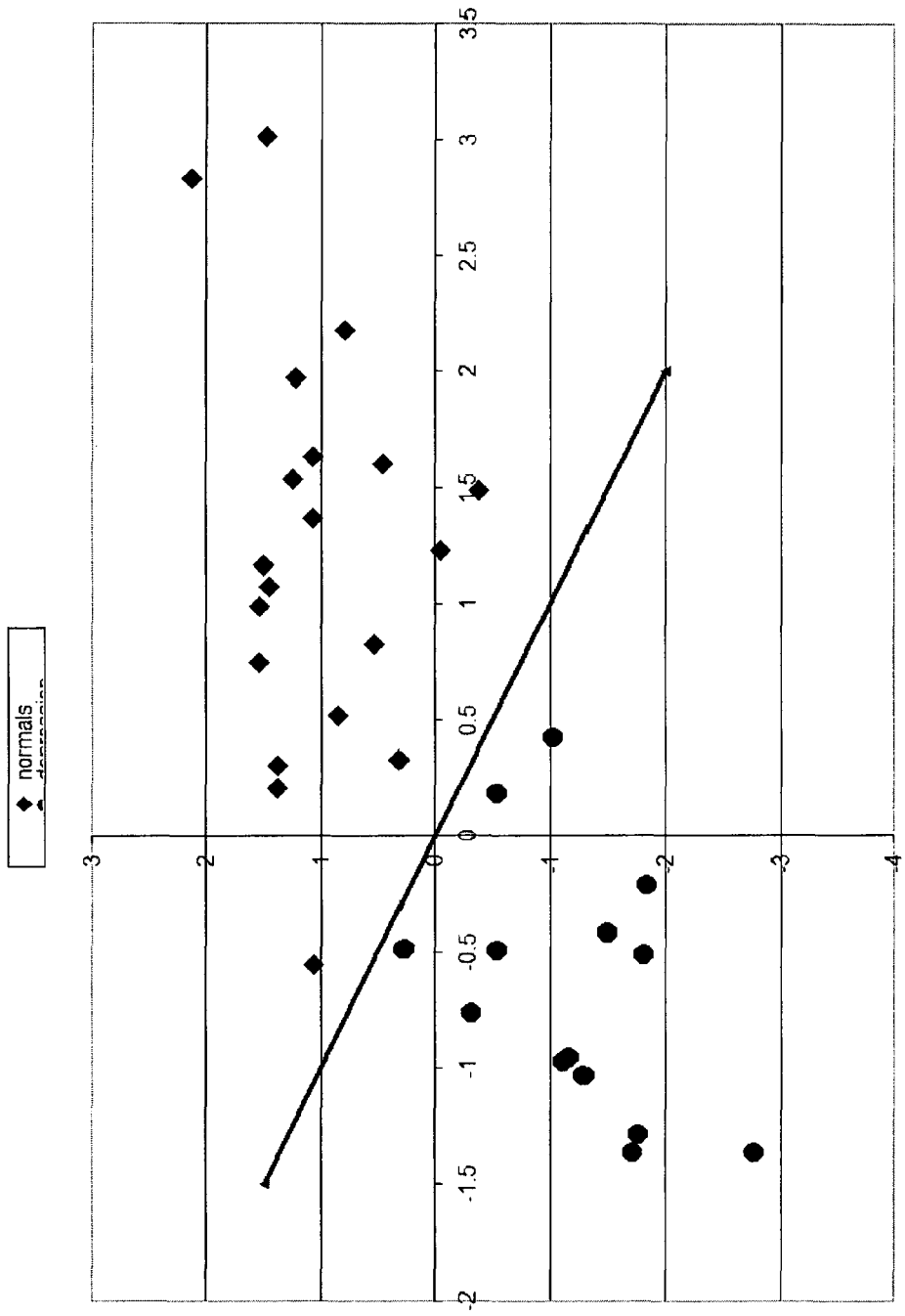
FIG. 12 is a diagram of a biomarker display generated by the EVestG system for patients with depression.
Figure 13:
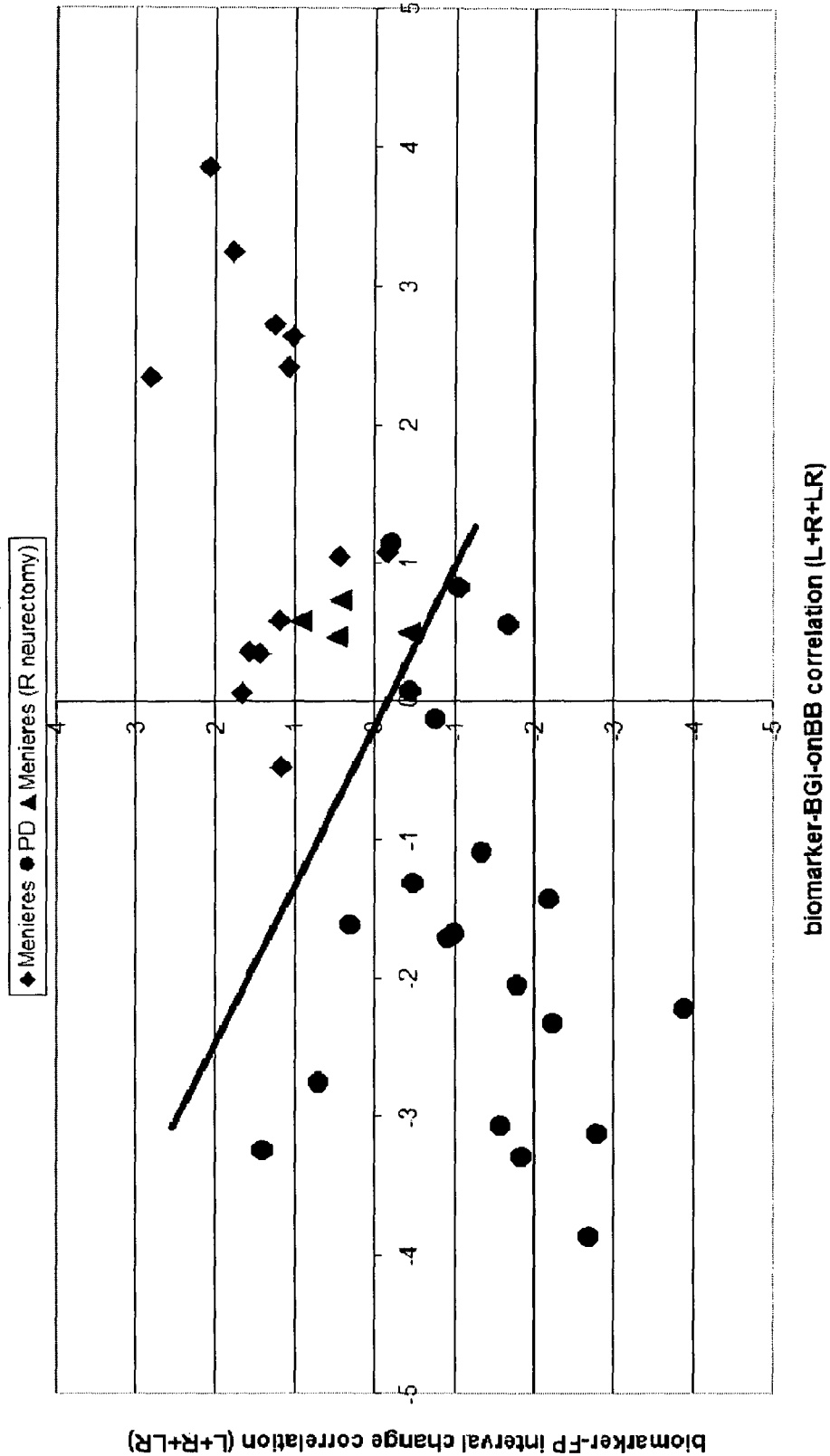
FIG. 13 is a diagram of a biomarker display generated by the system for patients with Meniere's disease and Parkinson's disease.
Figure 14:
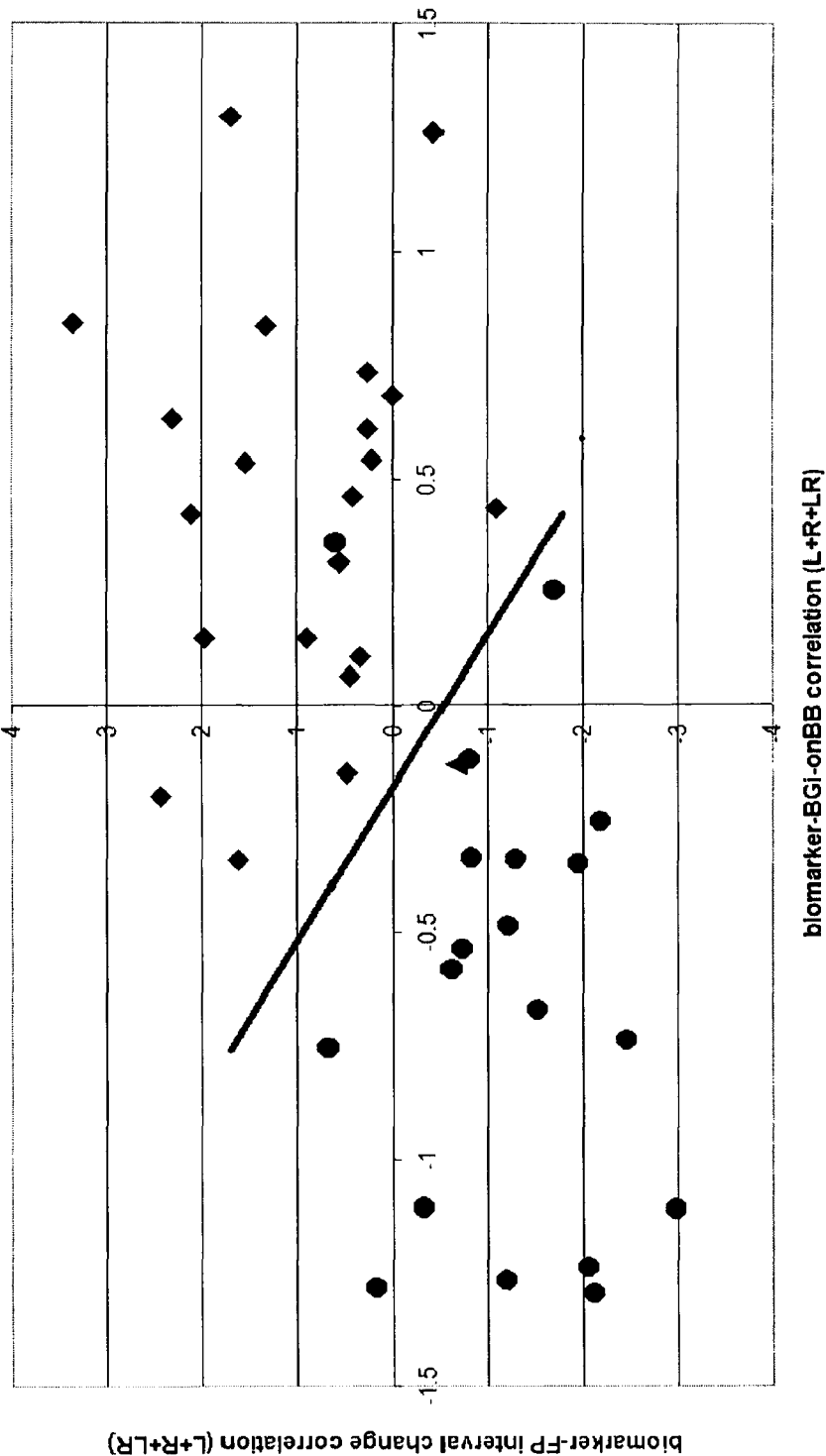
FIG. 14 is a diagram of a biomarker display generated by the system for patients with Parkinson's disease and schizophrenia.
Figure 15:
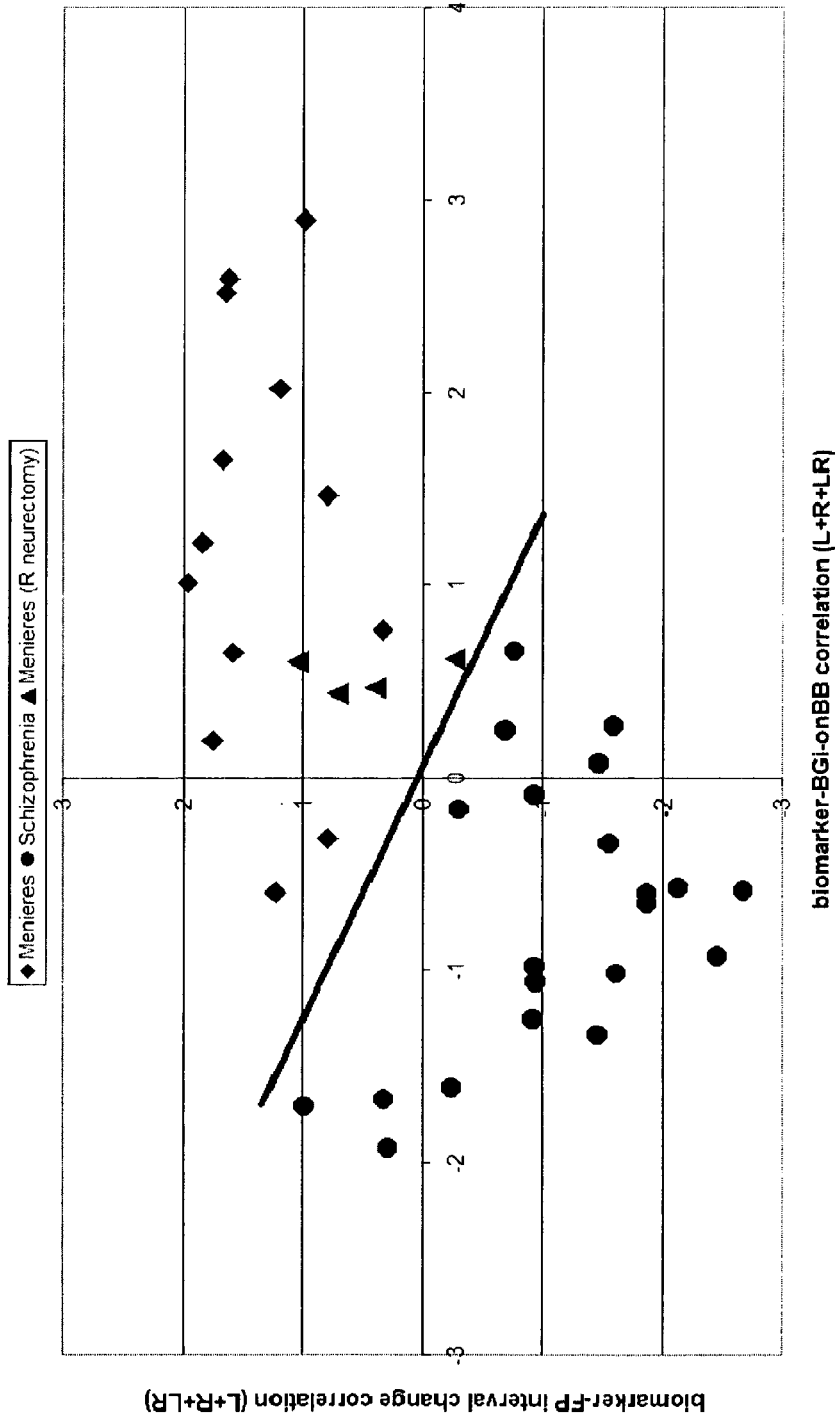
FIG. 15 is a diagram of a biomarker display generated by the system for patients with Meniere's disease and schizophrenia.
Figure 16:
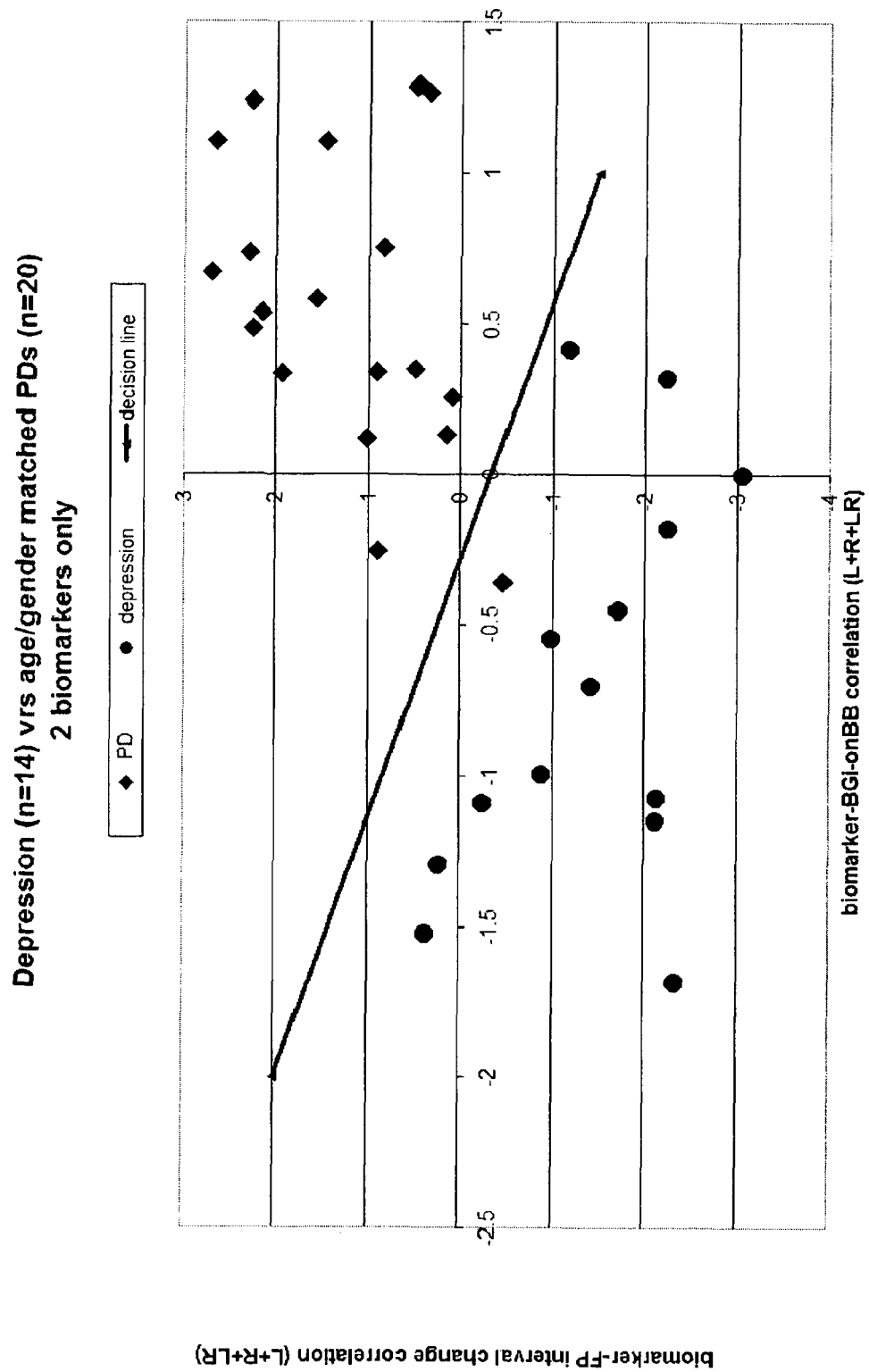
FIG. 16 is a diagram of a biomarker display generated by the system for patients with depression, bipolar disorder and Parkinson's disease.
Figure 17:
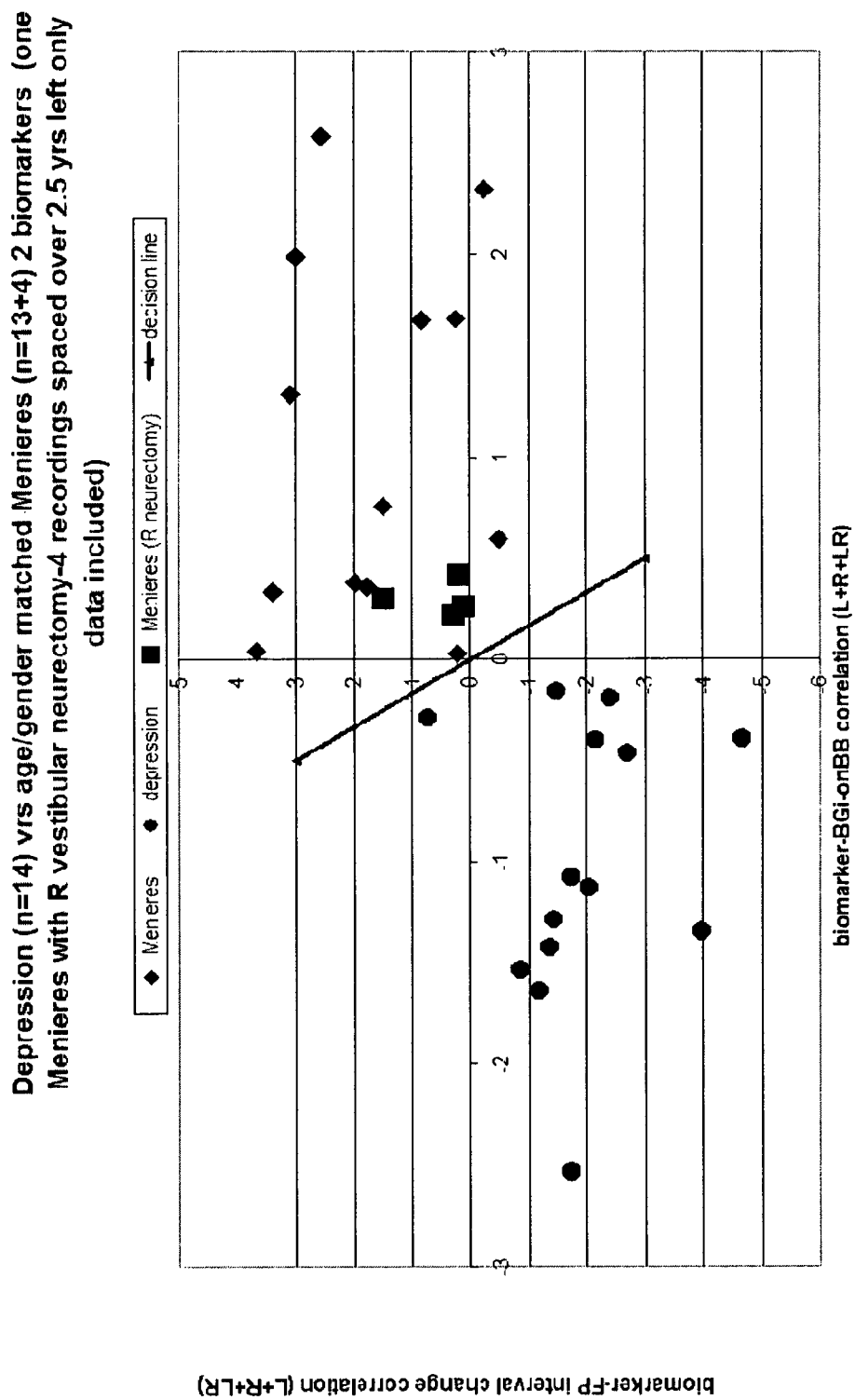
FIG. 17 is a diagram of a biomarker display generated by the system for patients with depression, bipolar disorder and Meniere's disease.
Figure 18:
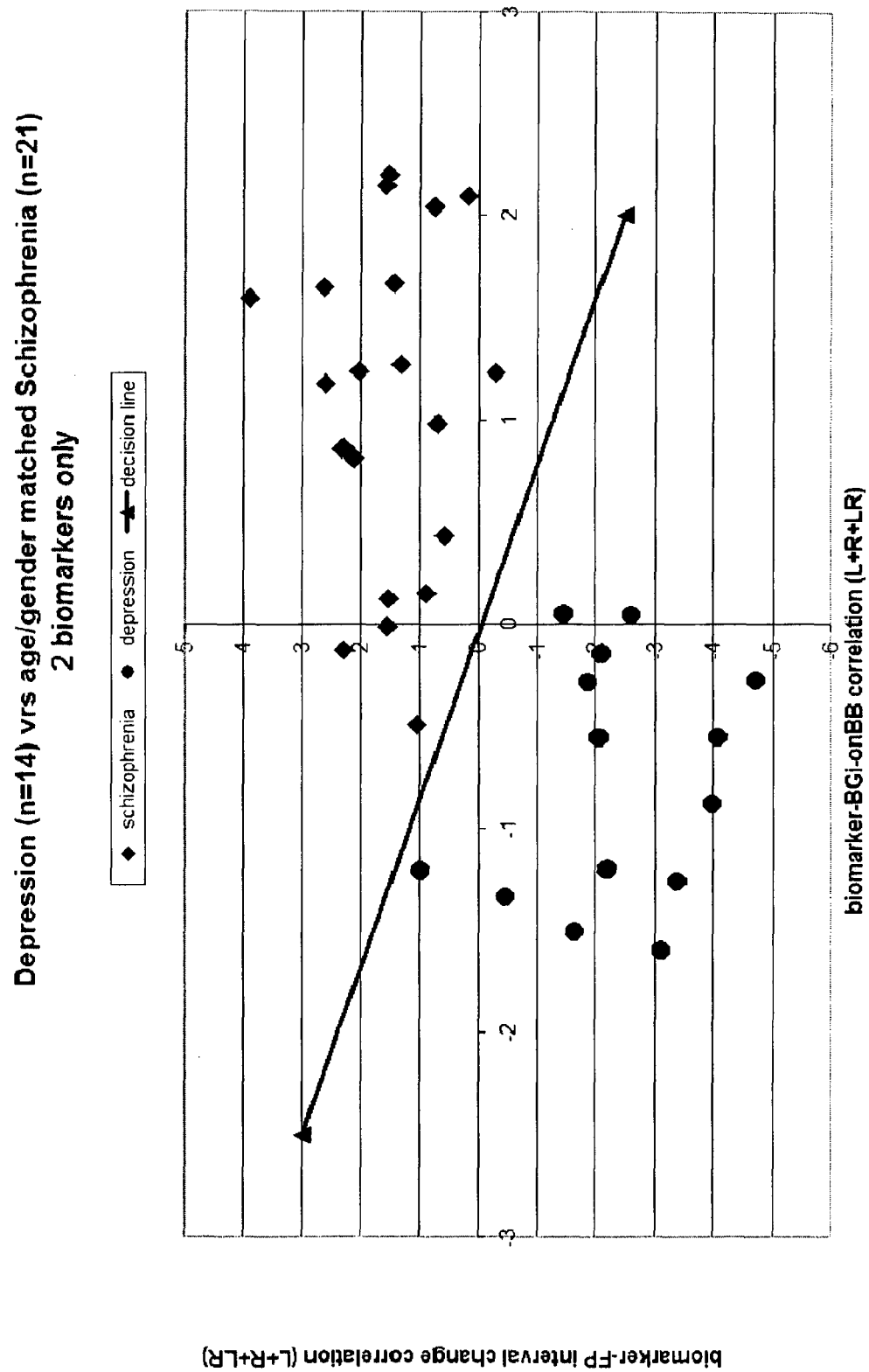
FIG. 18 is a diagram of a biomarker display generated by the system for patients with depression and schizophrenia.

FIGS. 9 to 21 show biometric displays generated by the graphic display module 30 and the analysis module 28 using the display point data for the horizontal and vertical axes. The plots were obtained by correlating each of the subjects of the control and pathology groups with the average responses. For example, FIG. 9 shows the separation between the members of a control group, and the members of a pathology group known to exhibit Parkinson's disease. FIG. 10 shows the separation between the members of a control group and the members of a group known to have Meniere's disease. FIG. 11 shows the separation between an age and gender match control group and members of a population known to exhibit Schizophrenia. FIG. 12 shows the separation between the members of an age and gender match control group and a group known to exhibit depression. FIG. 13 shows the separation between subjects in a group known to exhibit Meniere's disease and those known to exhibit Parkinson's disease. FIG. 14 shows a biometric display illustrating the separation between a group known to exhibit Schizophrenia and a group known to exhibit Parkinson's disease. FIG. 15 shows a biometric display illustrating the separation between a group known to exhibit Meniere's disease and a group known to exhibit Schizophrenia. FIG. 16 shows a separation between a group known to exhibit depression and a group known to exhibit Parkinson's disease and four patients known to exhibit bipolar disorder. FIG. 17 shows the separation between a group known to exhibit depression, a group known to exhibit Meniere's disease and four patients known to exhibit bipolar disorder. FIG. 17 also shows four points obtained from four recording sessions done for a patient known to have Meniere's disease and who has been treated by a right ear vestibular neurectomy procedure, which involves severing the vestibular nerve. FIG. 18 shows the separation between a group known to exhibit depression and a group known to exhibit Schizophrenia.

Figure 19:
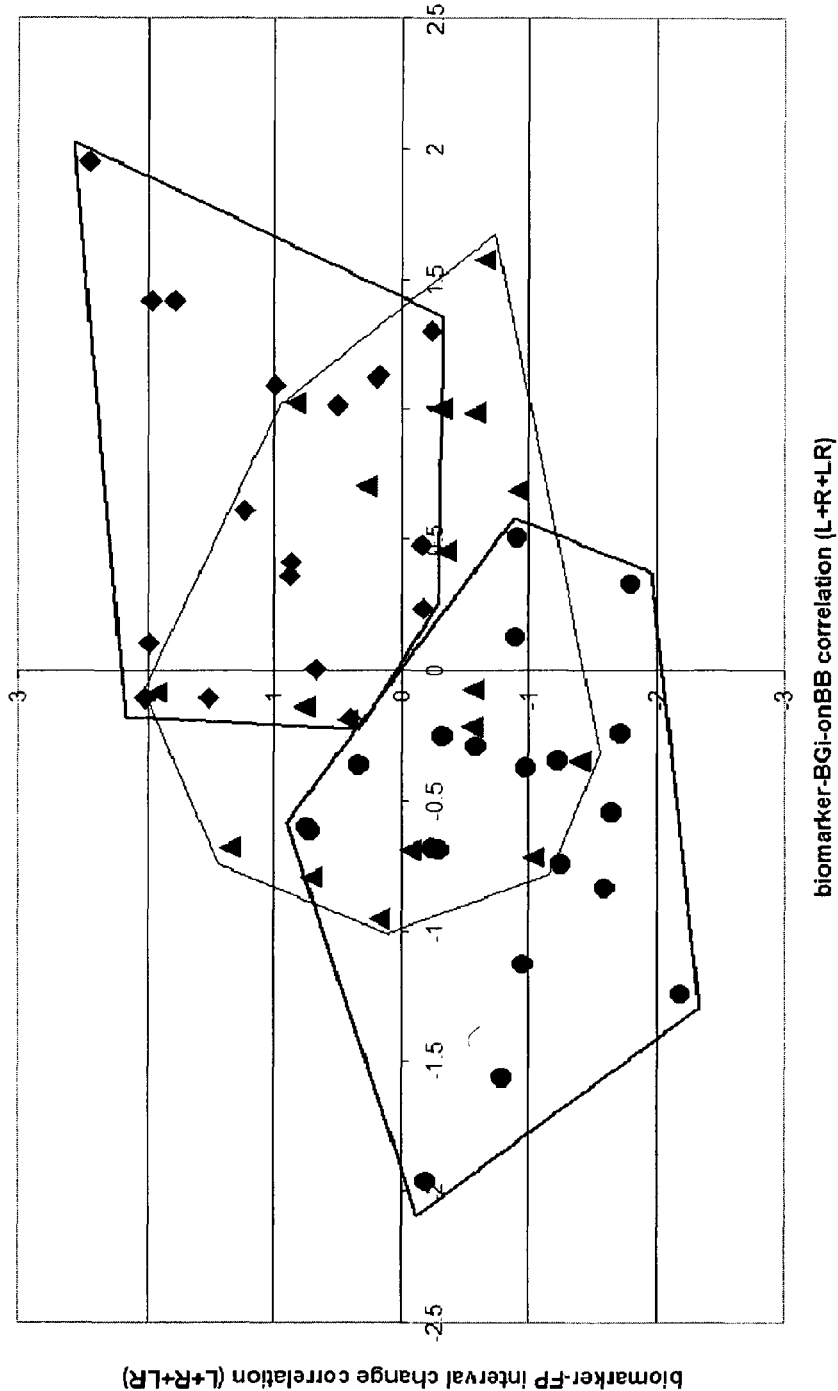
FIG. 19 is a diagram of a biomarker display generated by the system comparing patients with Parkinson's disease before and after medication, and normal control patients.

FIG. 19 shows a biometric display of the display points obtained for members of an age and gender matching control group, the members of a group known to exhibit Parkinson's disease before medication, and the members of the same group after being medicated by L-Dopa medication. The effects of the medication can be seen with the medicated group moving towards the control group.

Figure 20:
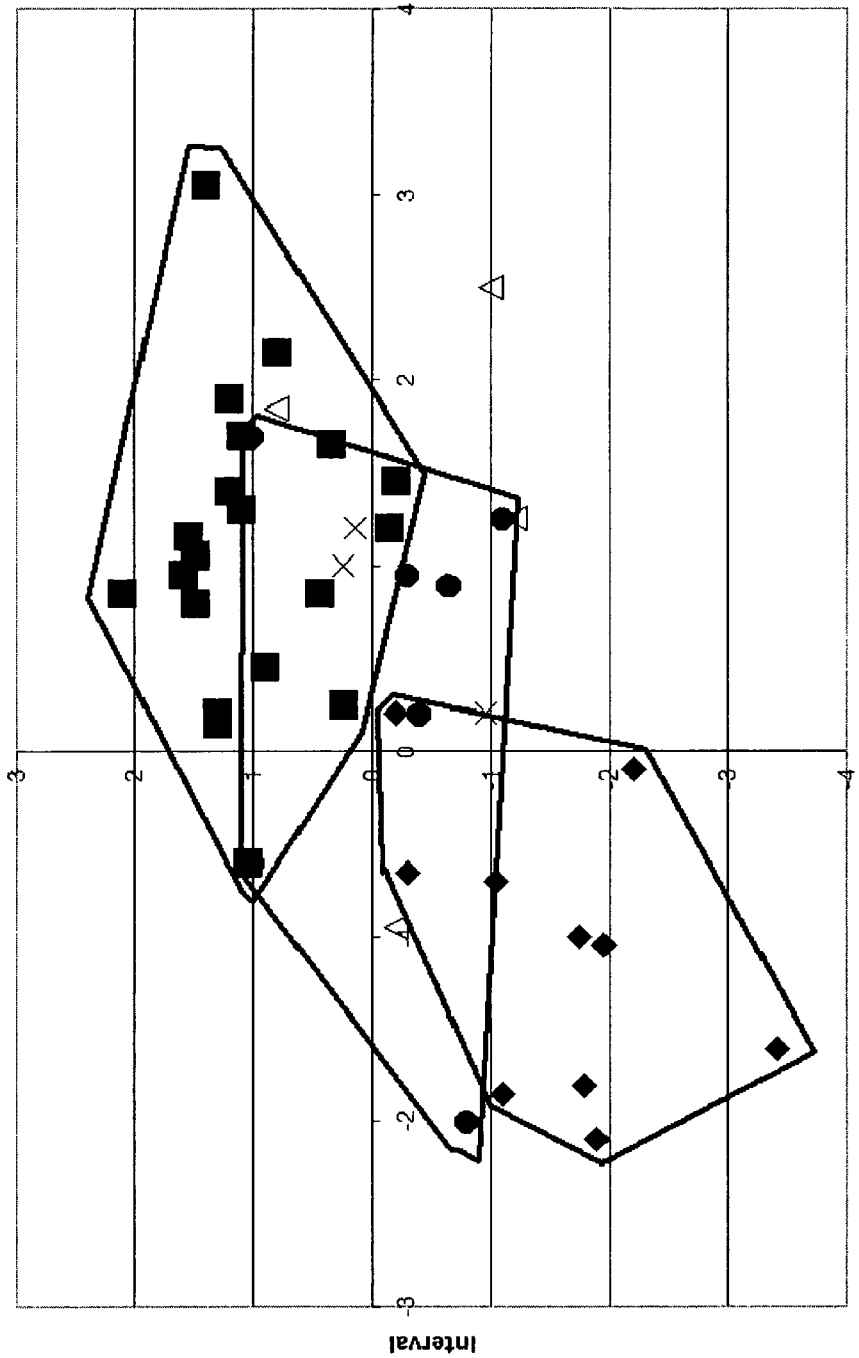
FIG. 20 is a diagram of a biomarker display generated by the system for comparing control patients with patients with depression and bipolar disorder both before and after treatment using transcranial magnetic stimulation (TMS)

FIG. 20 shows a biometric display of display points obtained for members of an age and gender matched control group, the members of a group known to exhibit depression before treatment, members of a group known to exhibit bipolar disorder before treatment, and the members of the same two groups after being treated using transcranial magnetic stimulation (TMS). The effects of the TMS treatment can be seen with the treated groups moving towards the control group.

Figure 21:
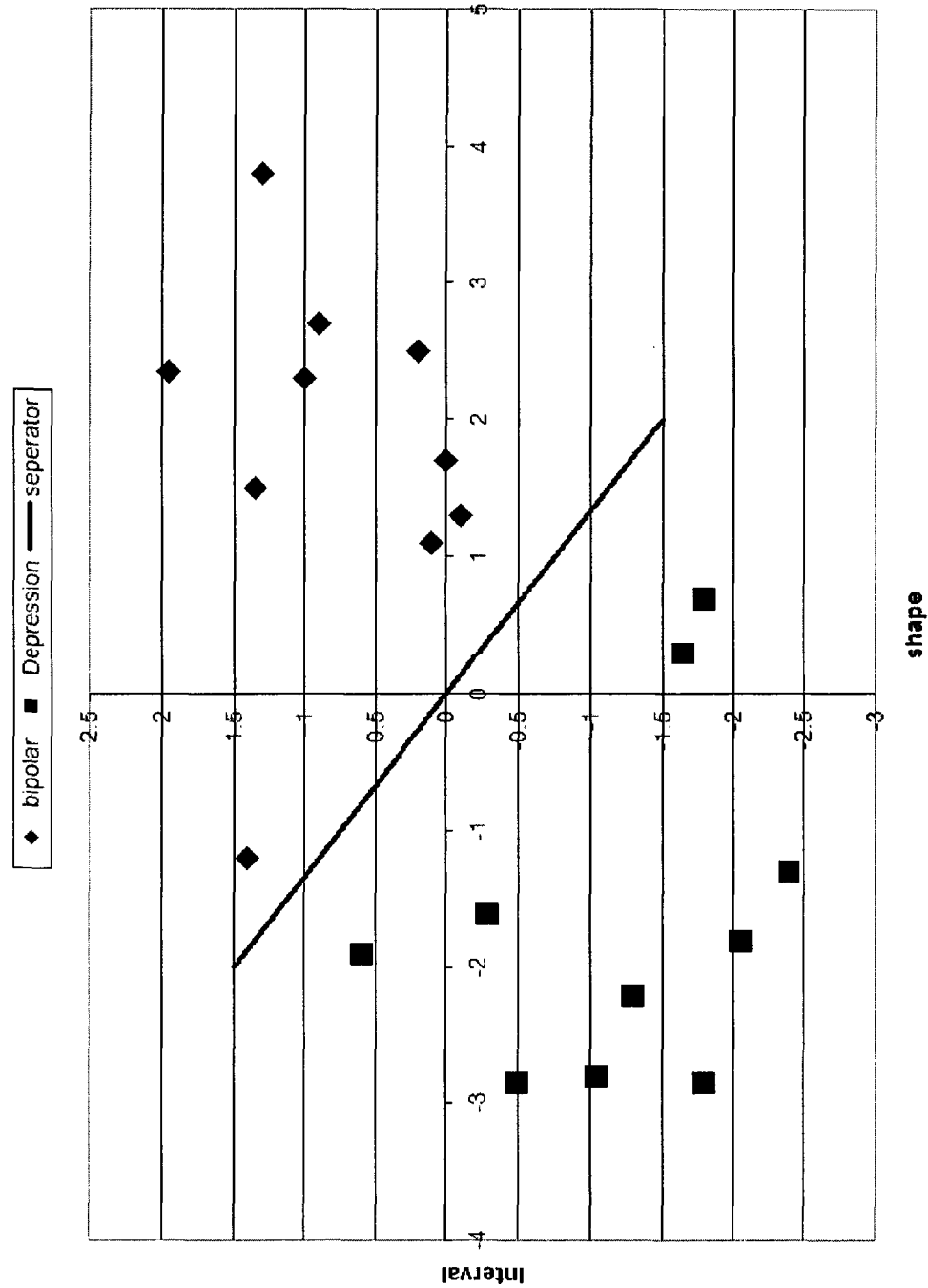
FIG. 21 is a diagram of a biomarker display generated by the system for patients with a major depressive disorder (e.g. depression) and bipolar disorder.

FIG. 21 shows separation between a group known to exhibit a major depressive disorder (e.g. depression) and a group known to exhibit bipolar disorder.

Generation of the biometric displays by the neural analysis system is particularly advantageous as displays can be produced to distinguish between subjects exhibiting a range of CNS disorders or conditions, and the effect of medication, without invasive techniques.

Many modifications will be apparent to those skilled in the art without departing from the scope of the present invention, as hereinbefore described, with reference to the accompanying drawings.

The claims defining the invention are as follows:
1. A neural analysis system, including:
a computer system comprising a processor and a display device, the computer system configured to:
extract neural event data and generate therefrom Sp/Ap curve data and field potential data for background and initial response segments obtained from a person;
correlate the Sp/Ap curve data and field potential data with pathology data for a condition, the pathology data comprising Sp/Ap curve data and field potential data for background and initial response segments from a population known to exhibit said condition;
generate from the correlation biomarker data points for axes of a biomarker display wherein one of said axes represents the correlation between the Sp/Ap curve data for the patient and the population, and the other of said axes represents the correlation between the field potential data for the patient and the population; and display on the display device the axes with said biomarker data points plotted relative to said axes for use in assessing said person relative to said condition.

2. The neural analysis system as claimed in claim 1, wherein the background and initial response segments include data obtained from the right and left ears in response to a stimulus.

3. The neural analysis system as claimed in claim 2, wherein the background and initial response segments are obtained for ipsilateral and contralateral tilts.

4. The neural analysis system as claimed in claim 1, wherein for the Sp/Ap curve data the segments are DC filtered.

5. The neural analysis system as claimed in claim 1, wherein for the field potential data the segments are high pass filtered to remove DC artefacts.

6. The neural analysis system as claimed in claim 1, wherein the computer system is additionally configured to generate correlation coefficient data for said person representing a measure of similarity with the pathology data for said condition, and correlation data for said person representing a measure of a similarity with neural event data obtained from a control population, and said points represent the difference between the correlation data associated with the pathology data and the correlation data associated with the control population.

7. The neural analysis system as claimed in claim 1, wherein said condition is a central nervous system condition, such as Parkinson's Disease, Schizophrenia, Depression, Meniere's Disease or Bipolar Disorder.

8. The neural analysis system as claimed in claim 1, wherein the computer system additionally configured to generate spectrograms for the background and initial response segments obtained from the person, and to correlate the spectrograms with spectrograms obtained from a population known to exhibit said condition and to generate a biomarker data point for another axis of the display.

9. The neural analysis system as claimed in claim 1, wherein the computer system comprises an element of a electrovestibulography (EVestG) system.

10. A neural analysis method, performed by a computer system, including:
    generating, using the computer system, Sp/Ap curve data and field potential data for background and initial response segments obtained from a person;
    correlating, using the computer system, the Sp/Ap curve data and field potential data with pathology data for a condition, the pathology data comprising Sp/Ap curve data and field potential data for background and initial response segments obtained from a population known to exhibit said condition;
    generating, using the computer system, from the correlation biomarker data points for axes of a biomarker display wherein one of said axes represents the correlation between the Sp/Ap curve data for the patient and the population, and the other of said axes represents the correlation between the field potential data for the patient and the population; and
    generating, using the computer system, the biomarker display with said biomarker data points plotted relative said axes for use in assessing said person relative to said condition.

11. The neural analysis method as claimed in claim 10, wherein the background and initial response segments include data obtained from the right and left ears in response to a stimulus.

12. The neural analysis method as claimed in claim 11, wherein the background and initial response segments are obtained for ipsilateral and contralateral tilts.

13. The neural analysis method as claimed in claim 10, wherein for the Sp/Ap curve data the segments are DC filtered.

14. The neural analysis method as claimed in claim 10, wherein for the field potential data the segments are high pass filtered to remove DC artefacts.

15. The neural analysis method as claimed in claim 10, wherein said correlating includes generating correlation coefficient data for said person representing a measure of similarity with the pathology data for said condition, and correlation data for said person representing a measure of a similarity with neural event extractor data obtained from a control population, and said points represent the difference between the correlation data associated with the pathology data and the correlation data associated with the control population.

16. The neural analysis method as claimed in claim 10, wherein said condition is a central nervous system condition, such as Parkinson's Disease, Schizophrenia, Depression, Meniere's Disease or Bipolar Disorder.

17. The neural analysis method as claimed in claim 10, including generating spectrograms for the background and initial response segments obtained from the person and correlating said spectrograms with spectrograms obtained from a population known to exhibit said condition to generate a biomarker data point for another axis of the display.

18. The neural analysis method of claim 10, wherein the computer system comprises a computer readable storage device storing computer program code for use in executing the neural analysis method.

19. The neural analysis method as claimed in claim 10, wherein the computer system comprises an element of a electrovestibulography (EVestG) system.

* * * * *